United States Patent
Yokota et al.

(10) Patent No.: US 8,683,229 B2
(45) Date of Patent: Mar. 25, 2014

(54) DATA ENCRYPTION DEVICE

(75) Inventors: Kaoru Yokota, Hyogo (JP); Masao Nonaka, Osaka (JP); Yuichi Futa, Osaka (JP); Natsume Matsuzaki, Osaka (JP)

(73) Assignee: Panasonic Corporation, Osaka (JP)

( * ) Notice: Subject to any disclaimer, the term of this patent is extended or adjusted under 35 U.S.C. 154(b) by 644 days.

(21) Appl. No.: 12/933,437

(22) PCT Filed: Mar. 25, 2009

(86) PCT No.: PCT/JP2009/001313
§ 371 (c)(1),
(2), (4) Date: Sep. 20, 2010

(87) PCT Pub. No.: WO2009/119079
PCT Pub. Date: Oct. 1, 2009

(65) Prior Publication Data
US 2011/0022851 A1 Jan. 27, 2011

(30) Foreign Application Priority Data
Mar. 25, 2008 (JP) ................................ 2008-077315

(51) Int. Cl.
*G06F 11/30* (2006.01)
*G06F 12/14* (2006.01)
*G06F 7/04* (2006.01)
*G06F 17/30* (2006.01)
*H04K 1/00* (2006.01)
*H04L 9/08* (2006.01)
*H04N 7/16* (2011.01)

(52) U.S. Cl.
USPC .............. 713/193; 726/27; 380/270; 380/278

(58) Field of Classification Search
USPC .......... 726/26–30; 380/270, 277–286, 44–47, 380/28–30; 713/1, 171, 193–194, 300, 310, 713/320
See application file for complete search history.

(56) References Cited

U.S. PATENT DOCUMENTS

| | | | |
|---|---|---|---|
| 5,842,023 A * | 11/1998 | Tsumura ........................ | 717/170 |
| 6,375,082 B1 * | 4/2002 | Kobayashi et al. ............ | 235/492 |
| 2005/0278222 A1 * | 12/2005 | Nortrup .......................... | 705/17 |
| 2006/0018484 A1 * | 1/2006 | Yoshihiro et al. ............. | 380/277 |
| 2007/0210923 A1 * | 9/2007 | Butler et al. .................. | 340/572.8 |
| 2007/0244825 A1 * | 10/2007 | Semmer et al. ................. | 705/59 |

(Continued)

FOREIGN PATENT DOCUMENTS

| | | |
|---|---|---|
| CN | 1231459 | 10/1999 |
| CN | 101101637 | 1/2008 |

(Continued)

OTHER PUBLICATIONS

International Search Report issued Jun. 16, 2009 in International (PCT) Application No. PCT/JP2009/001313.

*Primary Examiner* — Philip Chea
*Assistant Examiner* — Trong Nguyen
(74) *Attorney, Agent, or Firm* — Wenderoth, Lind & Ponack, L.L.P.

(57) ABSTRACT

A portable data sensor tag includes a memory, a data communication circuit which receives a wireless activation signal from an external terminal and, in an operation using electromotive force generated by the received activation signal, receives an encryption key from the external terminal and stores the received encryption key in the memory. A power source supplies power, an insulator which switches a power supply from the power source from off to on, and a sensor circuit reads the encryption key from the memory, encrypts measured data using the read encryption key, and stores the encrypted measurement data in the memory. The sensor circuit operates using the power supplied from the power source after the power supply from the power source is switched on.

19 Claims, 27 Drawing Sheets

(56) References Cited

U.S. PATENT DOCUMENTS

| | | | |
|---|---|---|---|
| 2009/0058648 A1* | 3/2009 | Tuttle | 340/572.1 |
| 2009/0224884 A1* | 9/2009 | Tuttle | 340/10.1 |

FOREIGN PATENT DOCUMENTS

| | | |
|---|---|---|
| JP | 56-55919 | 5/1981 |
| JP | 11-272822 | 10/1999 |
| JP | 2002-230161 | 8/2002 |
| JP | 2005-348306 | 12/2005 |
| JP | 2006-072565 | 3/2006 |
| JP | 2006-197202 | 7/2006 |
| JP | 2008-065360 | 3/2008 |
| WO | 2006/095450 | 9/2006 |
| WO | WO 2006095450 A1 * | 9/2006 |

* cited by examiner

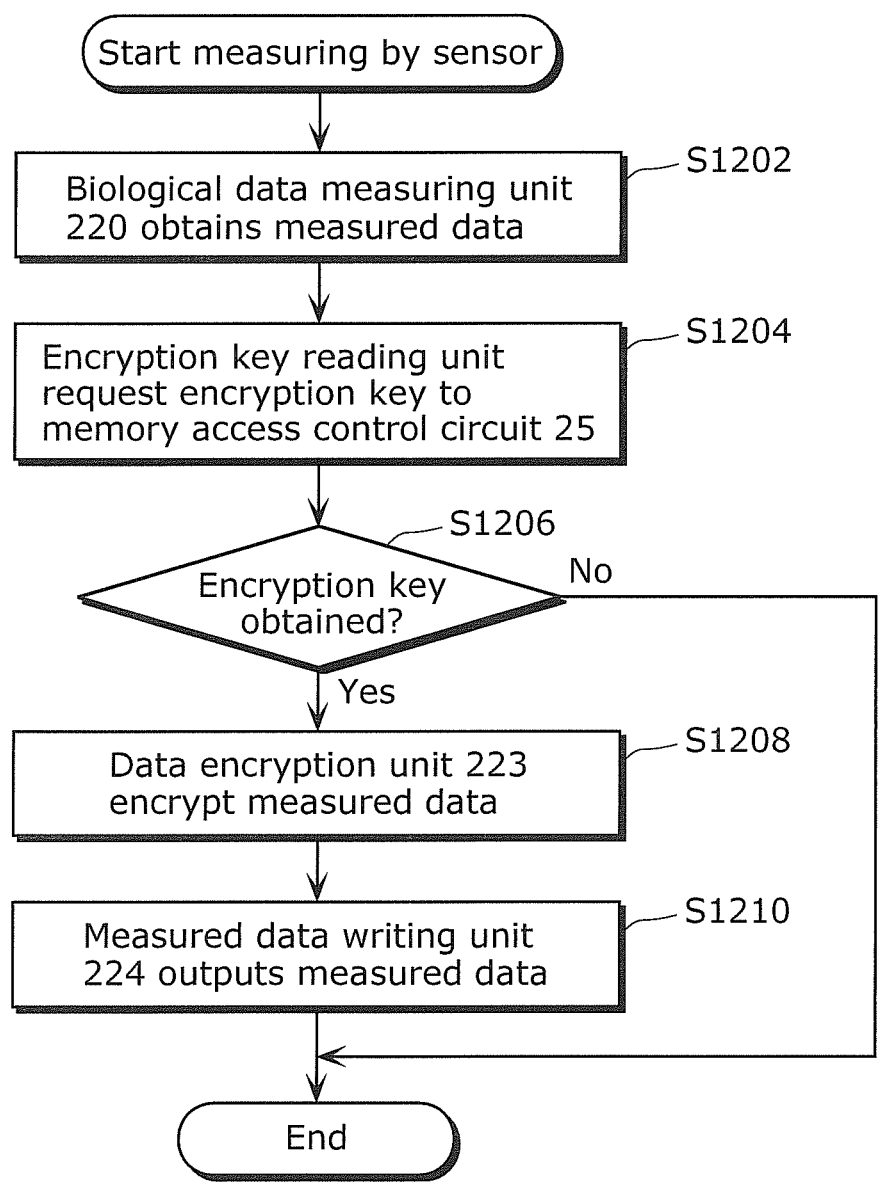

FIG. 24

| Data communication circuit 20 | Memory access control circuit 25 | Sensor circuit 22 |
|---|---|---|
| | Key can be set in initial state | Measurement stopped in initial state |
| S2 [Generate electromotive force] | | |
| S4 Obtain encryption key | | |
| | S6 Set encryption key (successful) | |
| | S40 Change mode | |
| | Key setting not possible afterwards | S38 Detect power turned on |
| | | Measurement subsequently start |
| | S44 Accumulate measured data | S42 Measurement by sensor |
| | | ※ Repeat measurement by sensor |
| S16 [Generate electromotive force] | | |
| S18 Obtain encryption key | | |
| | S20 Set encryption key (unsuccessful) | |
| S22 [Generate electromotive force] | | |
| S24 Request for obtaining data | | |
| | S28 Obtain data (Unsuccessful) | |
| | S44 Accumulate measured data | S42 Measurement by sensor |
| S22 [Generate electromotive force] | | |
| S24 Request for obtaining data | | |
| S30 Output data | S28 Obtain data (Successful) | |
| | | Measurement end |

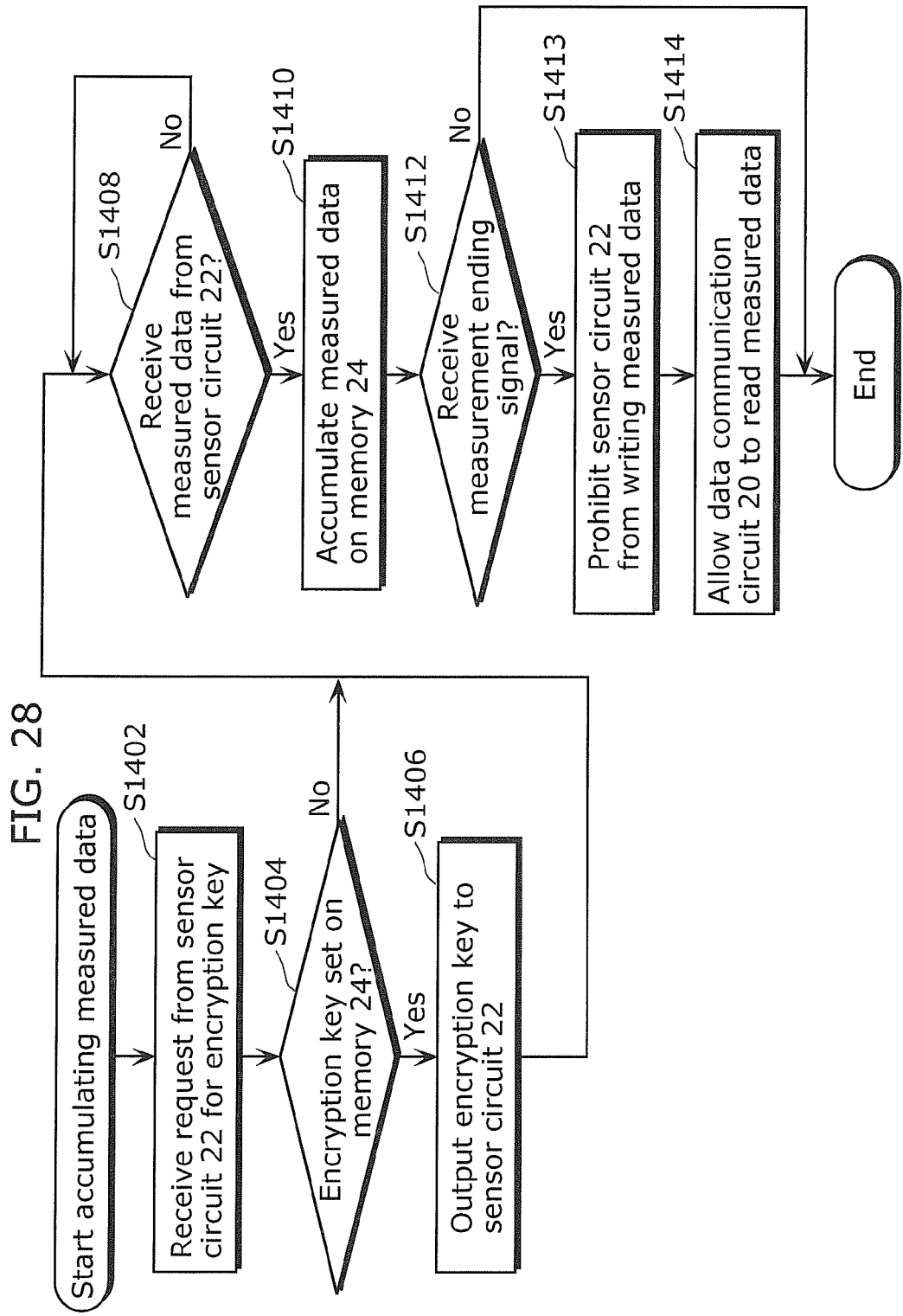

DATA ENCRYPTION DEVICE

BACKGROUND OF INVENTION

1. Technical Field

The present invention relates to a secure healthcare management system capable of protecting the confidentiality of health information in a healthcare management service in which health information such as body weight or blood pressure of a user measured by the user is received via a communication network and tips for health based on the health information are returned to the user.

2. Background Art

Tags that function as sensors such as thermal sensor, chemical sensor, pressure sensor, biosensor, and others, and that have communication function such as the Radio Frequency Identification (RFID) are in process for development. Furthermore, applications using the tags have been considered. The applications includes, for example, managing the temperature and humidity at the time of transporting fresh food or artwork by attaching tags that function as temperature sensor and humidity sensor. Furthermore, it is also possible to use the tags for managing health of patients who are required to measure body temperature, blood glucose level, and heart rate for a long term or regularly. Attaching a tag with the biological information measuring function (hereafter referred to as a "sensor tag") to a patient's body allows measuring biological information regularly. The biological information obtained through the measurement is accumulated in the sensor tag. After the measurement for a certain period ends, the sensor tag is removed from the patient's body, and the data accumulated inside is read out. Microminiaturization of the sensor tag enables measuring the biological information regularly without the patient realizing the presence of the sensor tag.

Upon using the sensor tag for the health management purpose, it is necessary to secure the confidentiality of the measured information accumulated in the sensor tag. More specifically, the measured biological information is personal information for the person being measured. There is a possibility that the measured data recorded within the sensor tag leaks when the sensor tag attached to the body becomes unstuck without noticed by the patient and picked up by a third party, or when the third party obtains the sensor tag because of insufficient management of the sensor tag after the data is read. A system in which the measured biological information is encrypted in the sensor tag and accumulated is necessary to prevent the data from leaking.

When encrypting the data within the sensor tag, the key needs to be set after shipment of the product (sensor tag). The sensor tags for health management purpose are purchased by hospitals and provided to patients from the hospitals. Thus, it is necessary to set different keys for each hospital such that, even when the key of a hospital leaks, there would be no risk on the leak of the measured information of the patients going to other hospitals. Accordingly, the sensor tags needs to be shipped and delivered to the hospitals with the key not set, so that the setting of the key can be made at each hospital.

The sensor tag has a battery built-in because the sensor tag must be supplied with power during measurement and there is no way to supply power to the sensor tag from outside of the sensor tag. In addition, the sensor tag must be microminiaturized in size, for it has to be constantly attached to the patient's body. Due to these limitations, it is difficult to provide a switch mechanism that turns on and off the power supply from the power source. Thus, the only available option is to insert an insulator between the battery and a sensor tag circuit, and to remove the insulator to turn on the power supply before use. In this case, however, it is difficult to insert the insulator that was once removed between the battery and the sensor tag again. In other words, once the power supply is turned on from off, the power supply cannot be turned off until the battery runs out.

The following is the overview of the processes for the conventional tags added with the encryption function in consideration of the above-described premises. First, the sensor tags are delivered to a hospital without the keys set. At the hospital, the power supply to the sensor tag is turned on, and the key is set. The hospital provides a patient with the sensor tag with the key set. The patient attaches the sensor tag, and measures the biological information. The sensor tag measures the biological information and encrypts the biological information using the key, and accumulates the information within the sensor tag while being attached to the body. After the measurement is completed, the patient hands in the sensor tag after the measurement to the hospital. The hospital reads out the encrypted measured biological information from the sensor tag, decrypts the information using the key held at the hospital, and obtains the biological information in plaintext. The biological information inside the sensor tag is encrypted. Thus, even if the sensor is obtained by the third party, there is no risk that the information leaks, since the third party does not have the key, and cannot obtain the decrypted biological information.

[Patent Literature 1] Japanese Unexamined Patent Application Publication No. 2006-197202

SUMMARY OF INVENTION

However, according to the conventional technology, it is necessary to turn on the power supply from the power source of the sensor tag upon setting the key. Thus, there is a problem that the battery is wasted before the measurement starts. Considering the necessity to miniaturize the sensor tag construction, a power switch structure simplified as much as possible, for example, a one-way switch may be used. However, with this structure, the power supply from the power source cannot be turned off once it is turned on. Thus, the power supply from the power source remains on after the key is set and until the patient attaches the sensor tag to his body, resulting in meaningless use of the battery. To avoid this problem, the hospital must set the key immediately before the sensor tag is handed to the patient, and the patient must attach the sensor tag immediately after receiving the tag, and start the measurement as soon as possible. However, the hospital cannot manage the stock by setting the key at one time after the sensor tags purchased in bulk is received, and cannot pass a number of sensor tags to a patient who is required to take continuous measurements for a long term, greatly increasing work for management operation in consequence.

The following describes another problem. Since the sensor tag is to be attached to the body, it is expected that the sensor tags are sterilized and shipped in package. In this case, the package must be is broken to turn on the power supply from the power source when setting the key at the hospital. However, breaking the sterilized package before use by the person to be measured who is a patient would cause a problem from a hygiene standpoint.

Patent Literature 1 discloses an electronic tag which includes a passive structure that receives the power energy supply through radio wave and an active structure that receives the power energy supply from an internal power source. In this electronic tag, the passive structure receives the identification information, and the active structure transmits the received identification information. In other words, in the electronic tag disclosed by Patent Literature 1, the passive structure is used for setting the identification information. Thus, it is not necessary to turn on the power supply from the internal power source. However, according to Patent Literature 1, only the identification information for items is set in the electronic tag. Patent Literature 1 fails to disclose methods for encrypting the data in the electronic tag or for setting the key. Accordingly, Patent Literature 1 cannot solve the abovementioned problem.

The present invention solves the abovementioned problem, and it is an object of the present invention to provide a sensor tag with encryption function that can remain sterilized immediately before the sensor tag is used, without increasing the work for management by the person who sets the key and the person who uses the sensor tag in a sensor tag system that requires key setting before use.

In order to achieve the object, the data encryption device according to the present invention is a portable data encryption device, including: a storage; a wireless communication circuit which receives a wireless activation signal from an external terminal, and, in an operation using electromotive force generated by the received activation signal, receives an encryption key from the external terminal and stores the received encryption key into the storage; a primary cell which supplies power; a switch which switches a power supply from the primary cell from off to on; and an encryption circuit which reads the encryption key from the storage, encrypts data using the read encryption key, and stores the encrypted data into the storage, the encryption circuit operating using the power supplied from the primary cell after the power supply from the primary cell is switched on.

According to this aspect, a wireless communication circuit receives the wireless activation signal from the external terminal, and, in an operation using electromotive force generated by the received activation signal, receives an encryption key from the external terminal and stores the received encryption key into the storage. The encryption circuit reads the encryption key, encrypts data using the read encryption key, and stores the encrypted data into the storage, while operating using the power supplied from the primary cell after the power supply from the primary cell is switched on. With this, when the wireless communication circuit receives the encryption key from an external device, the primary cell in the data encryption device is not used. Thus, even if it takes some time from the reception of the encryption key to encrypt the data, it is possible to prevent the primary cell in the device from being wasted when the encryption circuit encrypts the data.

Furthermore, even if a primary cell with a short life is used as the power source, the power from the primary cell is not used when the wireless communication circuit receives the encryption key from an external device. Thus, it is possible to prevent the power of the primary cell from being wasted when the encryption circuit encrypts the data.

Furthermore, it is possible to receive the encryption key wirelessly. Thus, the encryption key on the data encryption device can be set without breaking the sterilized package. Therefore, it is possible to maintain the data encryption device in a sterile condition immediately prior to the use.

Preferably, the data encryption device further includes a storage control unit which controls an access by the wireless communication circuit to the storage and an access by the encryption circuit to the storage, in which the storage control unit prohibits the wireless communication circuit from writing data into the storage, when the encryption circuit operates using the power supplied from the primary cell.

According to this aspect, when the encryption circuit operates with the power supplied from the primary cell, the storage control unit prohibits the wireless communication circuit from writing the data on the storage. With this, a new encryption key cannot be stored in the storage when the encryption on the data starts. Thus, it is possible to prevent the encryption key to be inadvertently rewritten when the encryption on the data starts.

More preferably, the encryption circuit is a sensor circuit, and measures biological data of a user of the data encryption device, reads the encryption key from the storage, encrypts the biological data using the read encryption key, and stores encrypted biological data into the storage.

According to this aspect, the encryption circuit is the sensor circuit which measures the biological data of the user of the data encryption device, and the sensor circuit can read the encryption key from said storage, encrypts the biological data, and stores the encrypted data into the storage. In this case, it is possible to use the data encryption device as a measuring device which measures the biological data of the user.

Furthermore, the data encryption device may further include an input unit which receives, as an input, biological data of a user from an external measuring device which measures the biological data, in which the encryption circuit encrypts the biological data as the data, and stores the encrypted biological data into the storage.

According to this aspect, the input unit receives the biological data as an input from the external measuring device which measures the biological data of the user, and the encryption circuit can encrypt the biological data as the data, and store the encrypted data in the storage. In this case, it is possible to use the data encryption device as a measuring device other than the measuring device which measures the biological data of the user.

Furthermore, when the power supply from the primary cell is switched on and the encryption circuit operates using the power supplied from the primary cell, with the encryption key not being stored in the storage, the encryption circuit may store the data into the storage without encryption.

According to this aspect, when the power supply from the primary cell is on and the encryption circuit operates with the power supplied from the primary cell, it is possible to store the data in the storage without encryption.

Furthermore, when the power supply from the primary cell is switched on and the encryption circuit operates using the power supplied from the primary cell, with the encryption key not being stored in the storage, the encryption circuit may discard the data, and may not store the data into the storage.

According to this aspect, when the power supply from said primary cell is on and the encryption circuit operates with the power supplied from the primary cell with the encryption key not stored in the storage, it is possible to discard the data, and not to store the data in the storage. In this case, the data is not stored in the storage unit without encryption, and thereby securing the confidentiality of the data.

Preferably, the switch switches the power supply from the primary cell unilaterally from off to on.

According to this aspect, the switch can switch the power supply from the primary cell only unilaterally from off to on. This simplifies the mechanism for switching on the power supply from the primary cell. Thus, it is possible to miniaturize the data encryption device.

More preferably, the primary cell and the encryption circuit are urged toward each other, and the switch is an insulator interposed between the urged primary cell and the urged encryption circuit.

According to this aspect, the switch can be an insulator interposed between the primary cell and the encryption circuit. In this case, pulling out the insulator from the data encryption device can switch on the power supply from the primary cell. As a result, it is possible to simplify the structure of the data encryption device while miniaturizing the device.

Preferably, the data is personal information of a user of the data encryption device.

According to this aspect, the data may be personal information of the user of the data encryption device.

Furthermore, the encryption circuit may be a sensor circuit which measures environment information around an item to which the data encryption device is attached, reads the encryption key from the storage, encrypts the environment information using the read encryption key, and stores the encrypted environment information into the storage.

According to this aspect, the encryption circuit may be a sensor circuit which measures the environment information around the item to which the data encryption device is attached. Thus, it is possible to read the encryption key from the storage, encrypt the environment information, and store the encrypted information in the storage. In this case, for example, it is possible to attach the data encryption device to the fresh food in transportation, and store the environment information such as the temperature, humidity, and luminance during the transportation in the data encryption device.

Furthermore, the wireless communication circuit may be a Radio Frequency Identification (RFID) communication circuit.

According to this aspect, the wireless communication circuit may be an RFID communication circuit. In this case, the data encryption device can be used as the RFID tag.

Furthermore, The data encryption device may further include an indicator which displays an indication that the encryption key is stored in the storage.

According to this aspect, providing the indicator which displays the indication that the encryption key is stored in the storage allows checking whether or not the encryption key is stored in the storage by seeing the data encryption device from outside. Thus, the user can use the data encryption device after checking whether or not the encryption key is stored in the storage. Thus, it is possible to secure the confidentiality of the data.

In addition, the data encryption device may further include a storage control unit which controls an access by the wireless communication circuit to the storage and an access by the encryption circuit to the storage, in which, when the encryption circuit operates using the power supplied from the primary cell, the storage control unit is configured to allow the encryption circuit to write data into the storage, and to prohibit the wireless communication circuit from writing data into the storage, the encryption circuit is a sensor circuit, and measures biological data of a user of the data encryption device, reads the encryption key from the storage, encrypts the biological data using the read encryption key, and stores encrypted biological data into the storage, the storage control unit prohibits the encryption circuit from writing the data into the storage when a request for obtaining the encrypted data stored in the storage is received from the wireless communication circuit, and the wireless communication circuit transmits the encrypted data stored in the storage to a predetermined destination, after the storage control unit prohibits the encryption circuit from writing the data into the storage.

According to this aspect, the storage control unit prohibits the encryption circuit from writing data into the storage when a request for obtaining the encrypted data stored in the storage is received from the wireless communication circuit. After the storage control unit prohibits the encryption circuit from writing the data into the storage, the wireless communication circuit reads the encrypted data stored in the storage and encrypted by the encryption circuit and transmits the read data to a predetermined destination. As a result, the encryption circuit does not write data on the storage while the wireless communication circuit transmits the data. Thus, it is possible to prevent the transmission data which is the encrypted data stored in the storage from leaking.

More preferably, when the request for obtaining the encrypted data stored in the storage is received from the wireless communication circuit, the storage control unit determines whether or not the encryption circuit has written the data into the storage within a predetermined period, and prohibits the encryption circuit from writing the data into the storage when it is determined that the encryption circuit has not written the data into the storage in the predetermined period.

According to this aspect, the storage control unit considers that the power of the primary cell is wasted when the encryption circuit has not written into the storage in a predetermined period, and prohibits the encryption circuit from writing the data on the storage. With this, when sufficient amount of encrypted data to be sent to the wireless communication circuit is stored in the storage from the storage, the wireless communication circuit can read the encrypted data and transmit the data to the predetermined destination. Thus, for example, it is possible to prevent, with a simple structure, the inefficient transmission of the encrypted data from the storage when the sufficient amount of the encrypted data to be transmitted to the wireless communication circuit is not stored, such as the case where the request from the wireless communication circuit to obtain the data immediately after the power supply from the primary cell is turned on.

More preferably, when the request for obtaining the encrypted data stored in the storage is received from the wireless communication circuit, the storage control unit determines whether or not the encryption circuit has written the data into the storage within a predetermined period, and when it is determined that the encryption circuit has written the data into the storage within the predetermined period, the storage control unit allows the encryption circuit to write the data into the storage, and maintains the prohibition against writing the data into the storage by the wireless communication circuit.

According to this aspect, the storage control unit determines that the primary cell still has some power left when the encryption circuit has written data on the storage within the predetermined period, and allows the encryption circuit to write the data into the storage, and maintain the prohibition on the wireless communication circuit from writing the data into the storage. With this, when the primary cell is determined to have some power left, the process for storing, into the storage, the encrypted data to be sent to the wireless communication circuit continues even if the request for obtaining the encrypted data stored in the storage is received from the wireless communication unit. Thus, for example, it is possible to prevent, with a simple structure, the inefficient transmission of the encrypted data from the storage when the sufficient amount of the encrypted data to be transmitted to the wireless communication circuit is not stored, such as the case where the request from the wireless communication circuit to obtain the data immediately after the power supply from the primary cell is turned on.

Furthermore, when the request for obtaining the encrypted data stored in the storage is received from the wireless communication circuit, the storage control unit is configured to output, to the encryption circuit, a predetermined signal for confirming that the encryption circuit is in operation, and determines whether or not the encryption circuit has responded within a predetermined period, and the storage control unit prohibits the encryption circuit from writing the data into the storage when it is determined that the response has not received within the predetermined period.

According to this aspect, when the response from the encryption circuit has not received within the predetermined period, the storage control unit considers that the power from the primary cell is wasted, and prohibits the encryption circuit from writing data into the storage. With this, when sufficient amount of encrypted data to be sent to the wireless communication circuit is stored in the storage, the wireless communication circuit can read the encrypted data and transmit the data to the predetermined destination. Thus, for example, it is possible to prevent, with a simple structure, the inefficient transmission of the encrypted data from the storage when the sufficient amount of the encrypted data to be transmitted to the wireless communication circuit is not stored, such as the case where the request from the wireless communication circuit to obtain the data immediately after the power supply from the primary cell is turned on.

More preferably, when the request for obtaining the encrypted data stored in the storage is received from the wireless communication circuit, the storage control unit outputs, to the encryption circuit, a predetermined signal for confirming that the encryption circuit is in operation, and determines whether or not the encryption circuit has responded within a predetermined period, and when it is determined that the response has received within the predetermined period, the storage control unit allows the encryption circuit to write the data into the storage, and maintains the prohibition against writing the data into the storage by the wireless communication circuit.

According to this aspect, the storage control unit determines that the primary cell still has some power left when the encryption circuit has responded within the predetermined period, and allows the encryption circuit to write the data on the storage, and maintain the prohibition on the wireless communication circuit from writing the data into the storage. With this, when the primary cell is determined to have some power left, the process for storing, into the storage, the encrypted data to be sent to the wireless communication circuit continues even if the request for obtaining the encrypted data stored in the storage is received from the wireless communication circuit. Thus, for example, it is possible to prevent, with a simple structure, the inefficient transmission of the encrypted data from the storage when the sufficient amount of the encrypted data to be transmitted to the wireless communication circuit is not stored, such as the case where the request from the wireless communication circuit to obtain the data immediately after the power supply from the primary cell is turned on.

Furthermore, the data encryption device may further include a storage control unit configured to control an access by the wireless communication circuit to the storage and an access by the encryption circuit to the storage, in which, when the encryption circuit operates using the power supplied from the primary cell, the storage control unit allows the encryption circuit to write data into the storage, and to prohibit the wireless communication circuit from writing data into the storage, the encryption circuit is a sensor circuit which measures biological data of a user of the data encryption device, reads the encryption key from the storage, encrypts the biological data using the read encryption key, stores encrypted biological data in the storage, and when the biological data is measured for a predetermined number of times, notifies of the storage control unit that the biological data has been measured for the predetermined number of times, the storage control unit prohibits the encryption circuit from writing the data into the storage when the notification that the biological data has been measured for the predetermined number of times is received, and the wireless communication circuit transmits the encrypted data stored in the storage to a predetermined destination, after the storage control unit prohibits the encryption circuit from writing the data into the storage.

According to this aspect, when the storage control unit receives the notification that the biological data has measured for the predetermined number of times, the storage control unit prohibits the encryption circuit from writing the data into the storage. The wireless communication circuit reads the encrypted data stored in the storage and encrypted by the encryption circuit and transmits the read data to a predetermined destination. As a result, the encryption circuit does not write data on the storage while the wireless communication circuit transmits the encrypted data. Thus, it is possible to prevent the transmission data which is the encrypted data stored in the storage from leaking.

Furthermore, the data encryption device may further include a storage control unit which controls an access by the wireless communication circuit to the storage and an access by the encryption circuit to the storage, in which, when the encryption circuit operates using the power supplied from the primary cell, the storage control unit allows the encryption circuit to write data into the storage, and prohibits the wireless communication circuit from writing data into the storage, the encryption circuit is a sensor circuit, and measures biological data of a user of the data encryption device, reads the encryption key from the storage, encrypts the biological data using the read encryption key, and stores encrypted biological data into the storage, the storage control unit prohibits the encryption circuit from writing the data into the storage after a predetermined has passed since the power supply from the primary cell has switched on, and the wireless communication circuit transmits the encrypted data stored in the storage to a predetermined destination, after the storage control unit prohibits the encryption circuit from writing the data into the storage.

According to this aspect, the storage control unit prohibits the encryption circuit from writing the data into the storage after the predetermined time has passed. The wireless communication circuit reads the encrypted data stored in the storage and encrypted by the encryption circuit and transmits the read data to a predetermined destination. As a result, the encryption circuit does not write data on the storage while the wireless communication circuit transmits the encrypted data. Thus, it is possible to prevent the transmission data which is the encrypted data stored in the storage from leaking.

Note that, the present invention may not only be implemented as the data encryption device including those characteristic processing units, but also as a data encryption method including the characteristic components included in the data encryption device as steps, or as a program causing a computer to execute the steps included in the data encryption method. Needless to say, such a program can be distributed through a recording medium, for example, a Compact Disc-Read Only Memory (CD-ROM) or a communication network such as the Internet.

According to the sensor tag of the present invention, even in the case of a small sensor tag in which the switch mechanism for freely switching between on and off cannot be embedded, it is not necessary to turn on the power supply from the embedded battery from off for setting the encryption key. This achieves and effect that the battery is not wasted before starting the measurement, which is described as the problem.

BRIEF DESCRIPTION OF DRAWINGS

FIG. 23 is a flowchart illustrating sensor measuring process according to the variation 3 of the first embodiment of the present invention in detail.

FIG. 24 is a flowchart illustrating the entire operation of the sensor tag 2 according to the second embodiment of the present invention in detail.

FIG. 28 is a flowchart illustrating a measured data accumulating process according to the second embodiment of the present invention in detail.

REFERENCE SIGNS LIST

Figure 1:
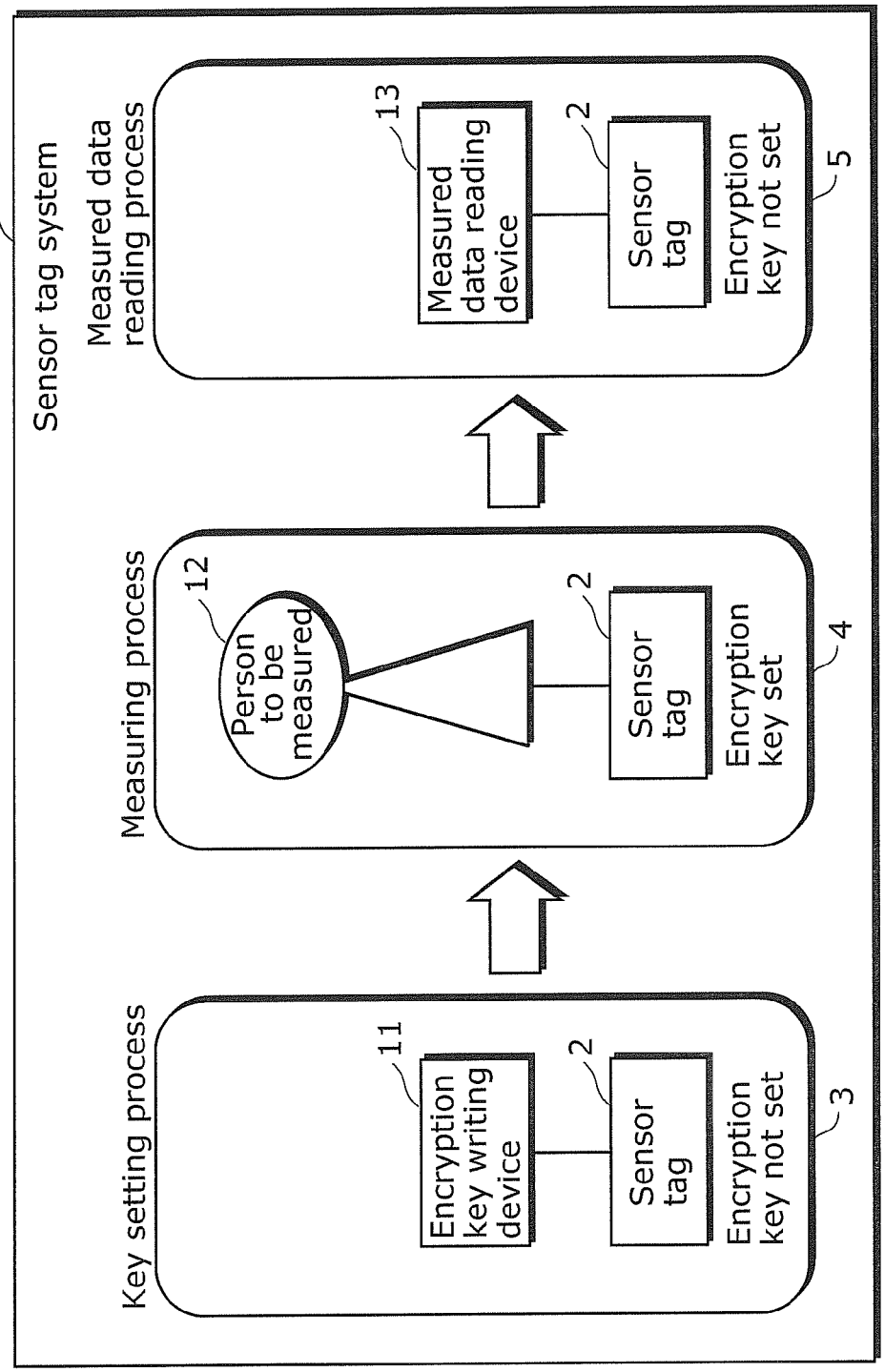
FIG. 1 is a block diagram illustrating the structure of a sensor tag system according to the first and second embodiments of the present invention.

1 Sensor tag system
2 Sensor tag
3 Key setting process
4 Measuring process
5 Measured data reading process
6 Group of encrypted measurement data
11 Encryption key writing device
12 Person to be measured
13 Measured data reading device
20 Data communication circuit
21 Antenna
22 Sensor circuit
23 Power source
24 Memory
25 Memory access control circuit
26 Memory access control rule updating unit
27 Insulator
28 Receiving circuit
29 Indicator
30 Electromotive force generating circuit
110, 130, 200 Data communication unit
111 Encryption key storage
112 Encryption key transmitting unit
113 ID receiving unit
114 ID transmitting unit
115, 131, 201 Authentication unit
132, 204 Measured data reading unit
133 Data decrypting unit
134 Measured data accumulating unit
135 Decryption key storage unit
202 Encryption key writing unit
203 ID writing unit
220 Biological data measuring unit
221 Timer unit
222 Encryption key reading unit
223 Data encrypting unit
224 Measured data writing unit
225 Power source status detecting unit

DETAILED DESCRIPTION OF INVENTION

First Embodiment

The following describes the first embodiment with reference to the drawings.

<Overview>

FIG. 1 is a block diagram illustrating the structure of the sensor tag system 1.

The sensor tag system 1 includes a sensor tag 2, an encryption key writing device 11, and a measured data reading device 13. Three processes are performed in the sensor tag system 1: a key setting process 3, a measuring process 4, and a measured data reading process 5.

The sensor tag 2 regularly measures the biological information of the person to be measured 12 such as body temperature, pulse, heart rate, heart sound, and others. The biological information that has been measured is encrypted using the encryption key set inside the sensor tag 2 in advance, and accumulated in the sensor tag 2.

The encryption key writing device 11 is a device for writing the encryption key on the sensor tag 2 that has no encryption key set.

The person to be measured 12 is a person whose biological information such as body temperature, pulse, heart rate, heart sound, and others is to be measured by the sensor tag 2.

The measured data reading device 13 is a device that reads, from the sensor tag 2 that finished measuring the biological information, the encrypted measurement data accumulated inside the sensor tag 2. The measured data reading device 13 also decrypts, using the decryption key, the encrypted measurement data that has been read to obtain the measurement data in plaintext.

The key setting process 3 is a process performed by the encryption key writing device 11 for setting the encryption key on the sensor tag 2 that has no encryption key set.

Figure 2:
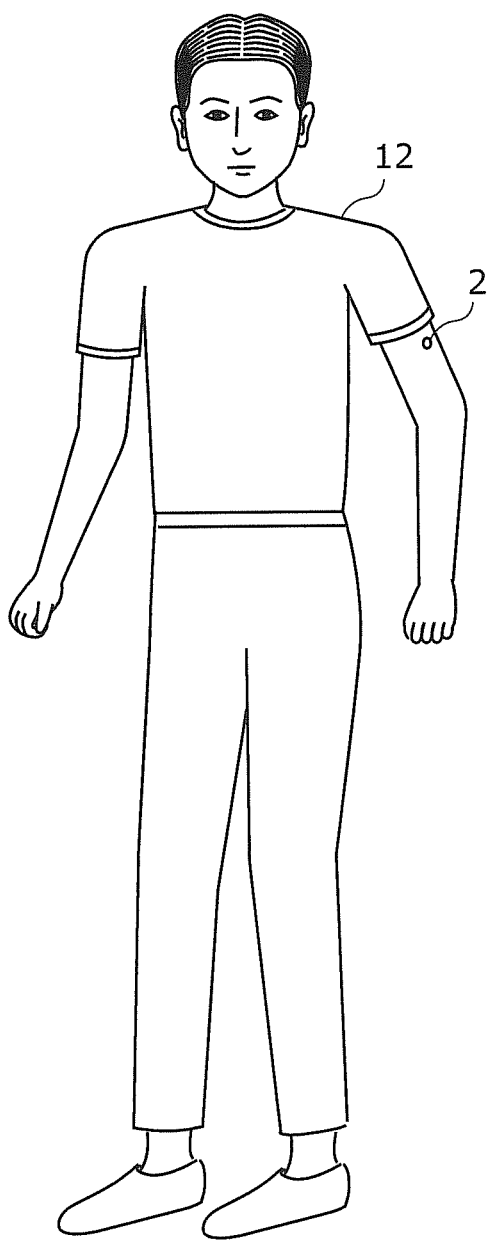
FIG. 2 is a diagram illustrating the embodiment of the sensor tag system according to the first and second embodiments.

The measuring process 4 is a process performed by the sensor tag 2 that is attached to the person to be measured 12 as illustrated in FIG. 2 and has the encryption key already set measures the biological information of the person to be measured 12, encrypts the biological information, and accumulates the biological information inside.

The measured data reading process 5 is a process performed by the measured data reading device 13 for reading the encrypted measurement data from the sensor tag 2 that finished measurement and decrypting the encrypted measurement data to obtain the measured data in plaintext.

The following describes one of the specific applications of the sensor tag system 1. The encryption key writing device 11 and the measured data reading device 13 are owned and managed by a hospital. The hospital purchases the sensor tags 2 that have no encryption key set from the manufacturer of the sensor tags. The hospital sets the encryption key on the sensor tag 2 that has been purchased, using the encryption key writing device 11. The sensor tag 2 that has the encryption key set is provided to the person to be measured 12 who is a patient of the hospital. The person to be measured 12 attaches the sensor tag 2 that has the encryption key set on his body at the right time, following the instruction from the hospital, and measures the biological information. The person to be measured 12 removes the sensor tag 2 that finished measurement from his body, and hand it in to the hospital. The hospital reads the encrypted measurement data from the sensor tag 2 that was handed in after measurement, using the measured data reading device 13. Subsequently, the encrypted measurement data is decrypted using the decryption key to obtain the measured data in plaintext. The hospital diagnoses the person to be measured 12 who is the patient, based on the obtained measurement data.

<Structure>

The following describes the structure of the sensor tag system 1.

1. Sensor Tag 2

Figure 3:
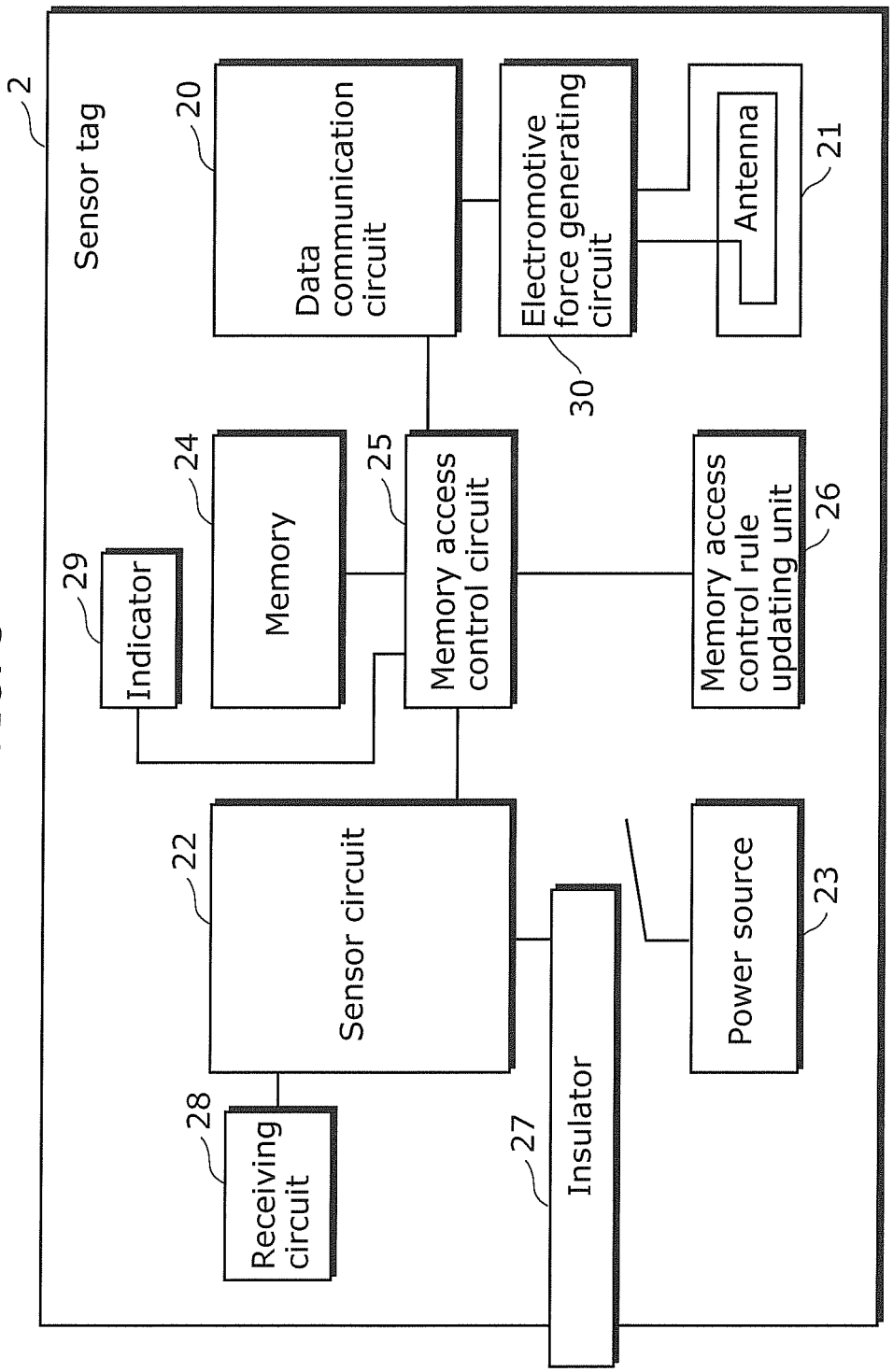
FIG. 3 is a block diagram illustrating the structure of a sensor tag system according to the first and second embodiments of the present invention.

FIG. 3 is a block diagram illustrating the structure of the sensor tag 2. As illustrated in FIG. 3, the sensor tag 2 includes a data communication circuit 20, an antenna 21, a sensor circuit 22, a power source 23, a memory 24, a memory access control circuit 25, a memory access control rule updating unit 26, an insulator 27, a receiving circuit 28, an indicator 29, and an electromotive force generating circuit 30.

The electromotive force generating circuit 30 is a circuit that generates electromotive force from the activation signal received by the antenna 21.

The data communication circuit 20 is a circuit that operates by the electromotive force generated by the electromotive force generating circuit 30, and is an RFID communication circuit. The data communication circuit 20 sets, on the memory 24, the encryption key transmitted from the encryption key writing device 11. In response to the request from the measured data reading device 13, the data communication circuit 20 also reads the encrypted measurement data accumulated in the memory 24, and transmits the encrypted measurement data to the measured data reading device 13. The internal structure of the data communication circuit 20 is to be described later.

The antenna 21 receives the signals from the encryption key writing device 11 and the measured data reading device 13 and outputs the received signals to the data communication circuit 20. Furthermore, the antenna 21 transmits the signals output from the data communication circuit 20 to the encryption key writing device 11 and the measured data reading device 13 through the radio wave, electromagnetic wave, or microwave, at a predetermined frequency.

The sensor circuit 22 is a circuit that operates using the power supplied from the power source 23. The sensor circuit 22 measures the biological information of the person to be measured 12 regularly, encrypts the biological information using the encryption key stored in the memory 24, and accumulates the encrypted data on the memory 24. The internal structure of the sensor circuit 22 shall be described later.

The power source 23 is an embedded primary cell of the sensor tag 2, and supplies power to the sensor circuit 22 and others.

The memory 24 is a nonvolatile data storage device shared by the sensor circuit 22 and the data communication circuit 20. The memory 24 stores data such as the encryption key data and the encrypted measurement data. The memory 24 receives the power supply from the sensor circuit 22 (that is, from the power source 23) when accessed by the sensor circuit 22, and receives the power supply from the data communication circuit 20 (that is, from the electromotive force generating circuit 30) when accessed by the data communication circuit 20.

The memory access control circuit 25 controls the access to the memory 24 from the sensor circuit 22 and the data communication circuit 20. The memory access control circuit 25 receives the data write request and the data read request from the sensor circuit 22 and the data communication circuit 20 to the memory 24, and determines whether or not to accept the request, based on the memory access control rule stored inside. When it is determined that the data write request or the data read request is accepted, the memory access control circuit 25 writes the predetermined data on the memory 24 or reads the predetermined data from the memory 24, according to the request. The memory access control circuit 25 receives the power supply from the sensor circuit 22 (that is, from the power source 23) when accessed by the sensor circuit 22, and receives the power supply from the data communication circuit 20 (that is, from the electromotive force generating circuit 30) when accessed by the data communication circuit 20.

The memory access control rule updating unit 26 updates the memory access control rule held in the memory access control circuit 25 when the sensor circuit 22 operates with the power supply from the power source 23 for the first time. The memory access control circuit 25 subsequently controls the data access from the sensor circuit 22 and the data communication circuit 20 based on the memory control rule that has been updated. One implementation of the memory access control rule updating unit 26 is that it is implemented as part of formatting program which is executed when the sensor circuit 22 operates for the first time, and executed as part of the initializing process for the sensor circuit 22.

When the sensor tag 2 is shipped, the insulator 27 is attached such that the electric connection between the sensor circuit 22 and the power source 23 is cut off. With this, the power supply to the sensor circuit 22 is shut off. The insulator 27 is attached such that the insulator 27 can be removed from outside of the sensor tag. For example, part of the insulator 27 is exposed to outside of the sensor tag 2. The person to be measured 12 can start the power supply from the power source 23 to the sensor circuit 22 such that the measurement of the biological information starts any time he prefers by removing the insulator 27. Note that, the sensor circuit 22 and the power source 23 are urged toward each other, and the insulator 27 switches the power supply from the power source 23 unilaterally from off to on. In other words, once the insulator 27 is removed, the insulator 27 cannot be inserted between the sensor circuit 22 and the power source 23. This allows simplifying and miniaturizing the structure of the sensor tag 2.

The receiving circuit 28 receives, as input, the biological data from the outside measuring device that measures the biological data of the person to be measured 12. The biological data that has been received is encrypted by the sensor circuit 22, and accumulated in the memory 24.

The indicator 29 indicates that the memory 24 stores the encryption key. The indicator 29 made of LED, for example, lights up, by the control of the memory access control circuit 25, when the encryption key is stored in the memory 24, and lights off when the encryption key is not stored. This prevents the user from inadvertently using the sensor tag 2 that has no encryption key set to start the measurement. Therefore, the confidentiality of the measured data is secured.

1.1 Data Communication Circuit 20

Figure 4:
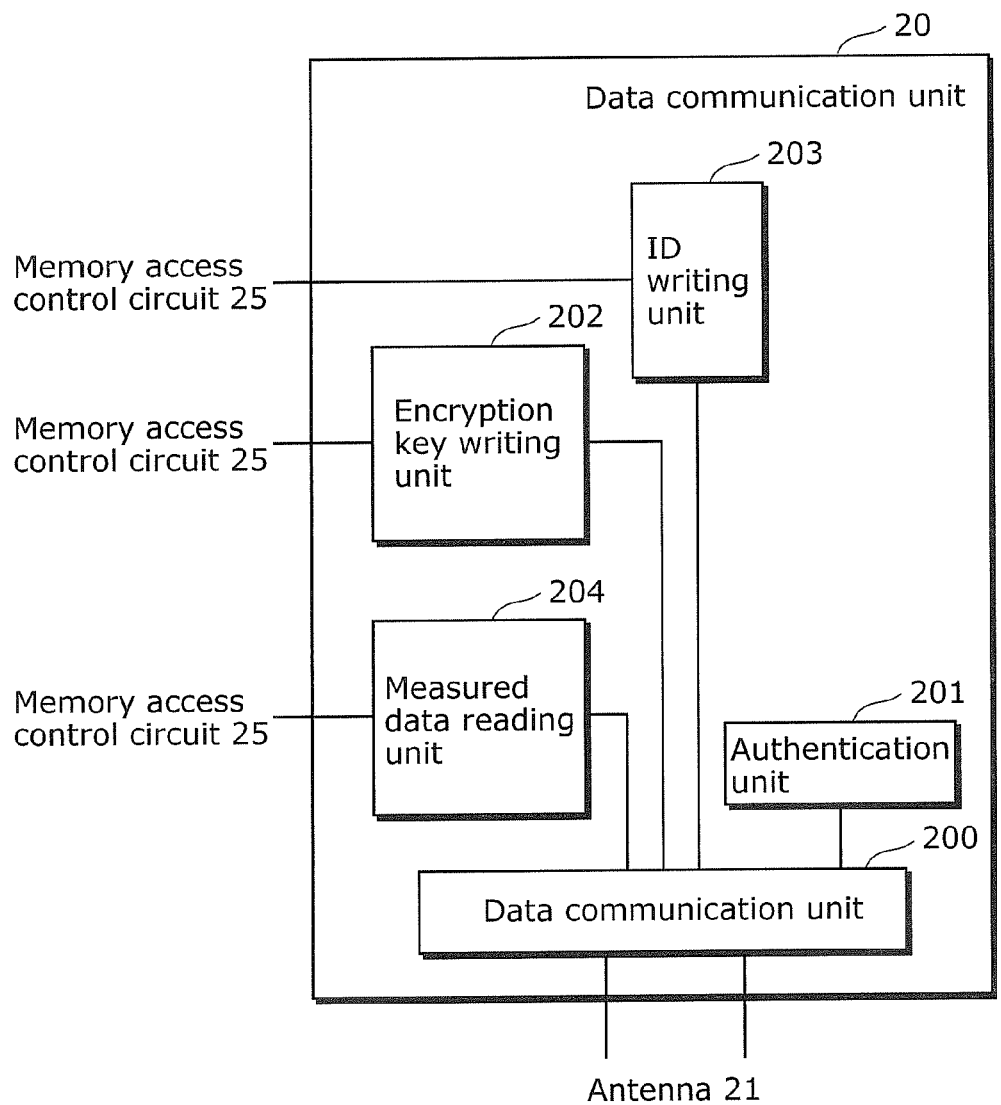
FIG. 4 is a block diagram illustrating the structure of a data communication circuit according to the first and second embodiments of the present invention.

FIG. 4 is a block diagram illustrating the structure of the data communication circuit 20. As illustrated in FIG. 4, the data communication circuit 20 includes a data communication unit 200, an authentication unit 201, an encryption key writing unit 202, an ID writing unit 203, and a measured data reading unit 204.

The data communication unit 200 receives data output from the antenna 21, which is received from the encryption key writing device 11 and the measured data reading device 13, and outputs an appropriate processing unit in the data communication circuit 20. The data communication unit 200 also receives data output from other processing units in the data communication circuit 20, and transmits the data to the encryption key writing device 11 and the measured data reading device 13 through the antenna 21.

The authentication unit 201 authenticates, using the data for verifying the authentication stored inside the authentication unit 201, the validity of the encryption key writing device 11 and the measured data reading device 13 that are attempting to transmit and receive data to and from the data communication circuit 20.

The encryption key writing unit 202 writes the encryption key data transmitted from the encryption key writing device 11 into the memory 24 through the memory access control circuit 25.

The ID writing unit 203 writes the ID data transmitted from the encryption key writing device 11 into the memory 24 through the memory access control circuit 25.

In response to a request from the measured data reading device 13, the measured data reading unit 204 reads the encrypted measurement data from the memory 24, and transmits the data to the measured data reading device 13 through the memory access control circuit 25.

1.2. Sensor Circuit 22

Figure 5:
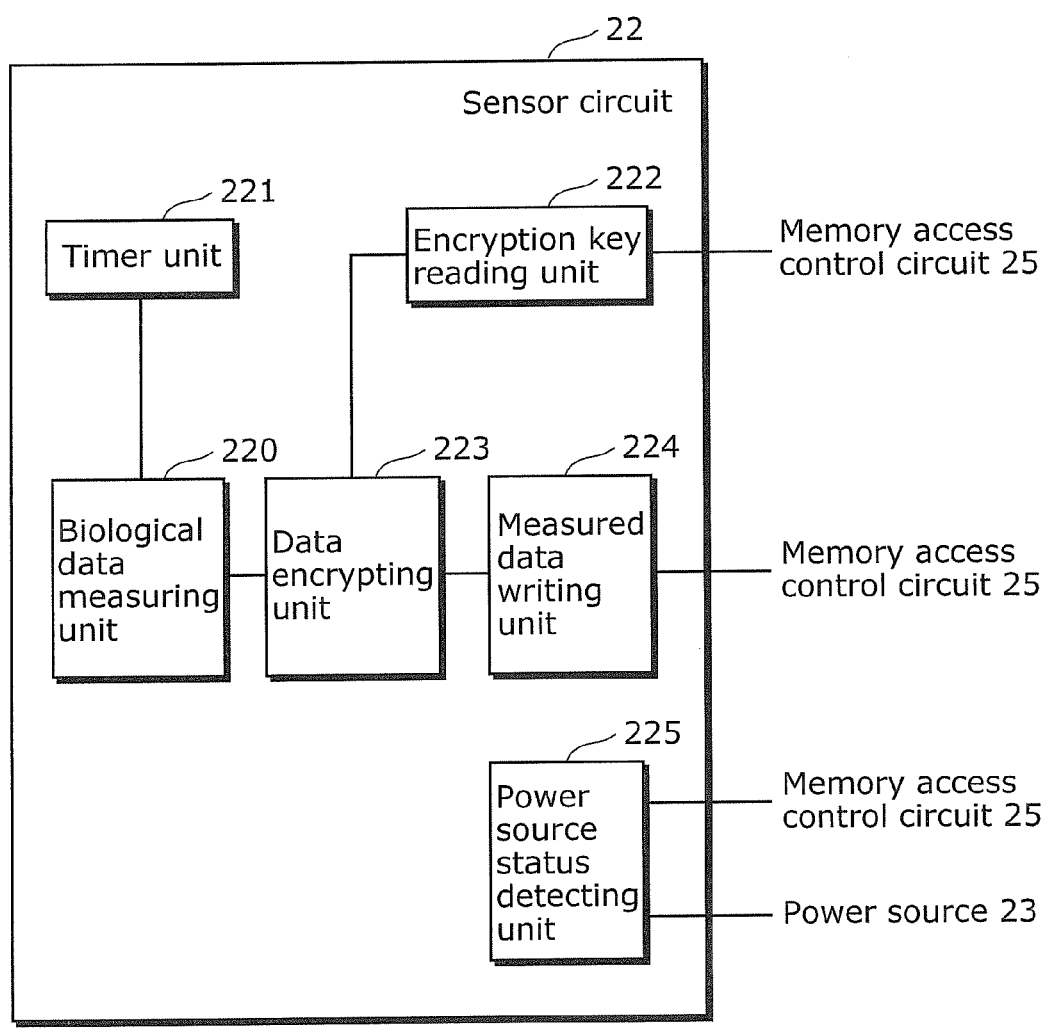
FIG. 5 is a block diagram illustrating the structure of a sensor circuit according to the first and second embodiments of the present invention.

FIG. 5 is a block diagram illustrating the structure of the sensor circuit 22. As illustrated in FIG. 5, the sensor circuit 22 includes a biological data measuring unit 220, a timer unit 221, an encryption key reading unit 222, a data encrypting unit 223, a measured data writing unit 224, and power source status detecting unit 225.

The biological data measuring unit 220 measures based on the count value on the timer unit 221, the biological information of the person to be measured at a predetermined interval to obtain the measured data, and outputs the measured data with the timer data (count value) to the data encrypting unit 223.

The timer unit 221 increments (adds one to) the count value at a constant interval, and notifies the biological data measuring unit 220 of the count value and that the count value reaches the predetermined value, each time the count value reaches to be a predetermined value.

The encryption key reading unit 222 reads the encryption key from the memory 24 through the memory access control circuit 25 in response to the request from the data encrypting unit 223, and outputs the encryption key to the data encrypting unit 223.

When receiving the measured data from the biological data measuring unit 220, the data encrypting unit 223 instructs the encryption key reading unit 222 to obtain the encryption key, and receives the encryption key. Subsequently, the data encrypting unit 223 encrypts, using the encryption key received from the encryption key reading unit 222, the measured data received from the biological data measuring unit 220 to obtain the encrypted measurement data, and outputs the encrypted measurement data to the measured data writing unit 224.

The measured data writing unit 224 writes the encrypted measurement data that is received from the data encrypting unit 223 into the memory 24 through the memory access control circuit 25.

The power source status detecting unit 225 detects the status of the power source 23; that is, whether or not the power supply from the power source 23 is on.

2. Encryption Key Writing Device 11

Figure 6:
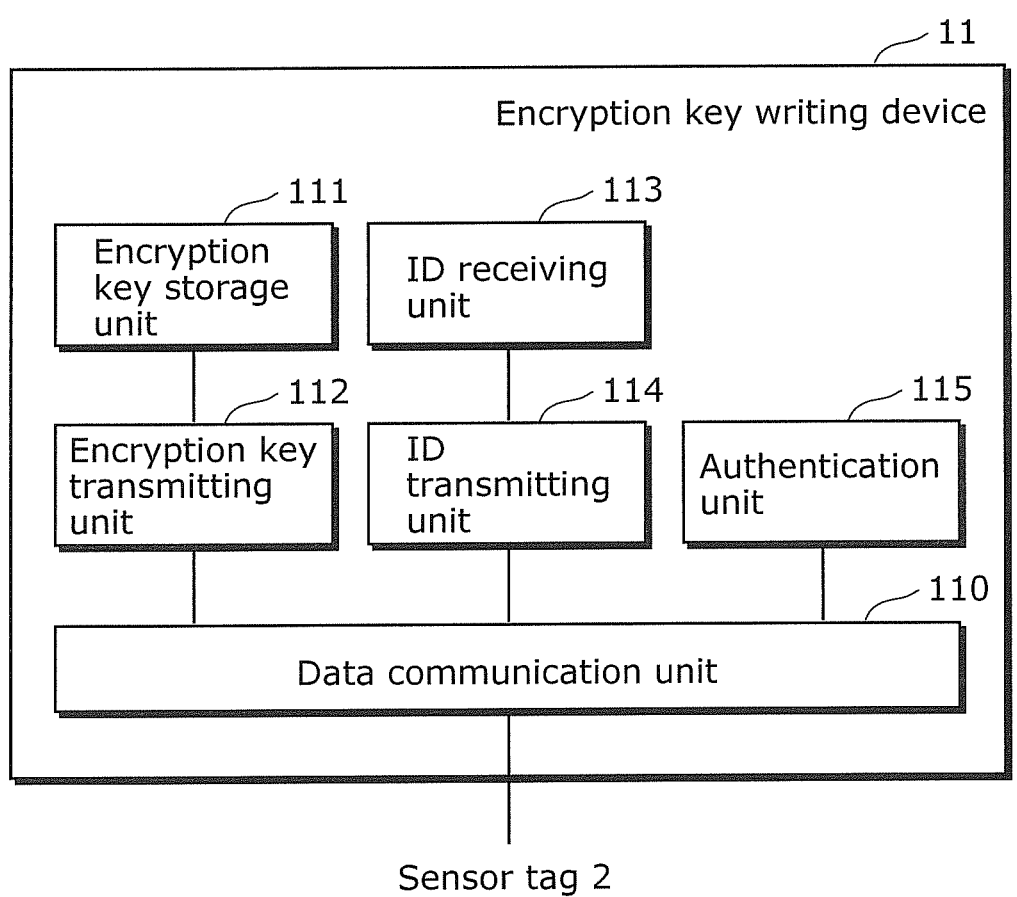
FIG. 6 is a block diagram illustrating the structure of an encryption key writing device according to the first and second embodiments of the present invention.

FIG. 6 is a block diagram illustrating the structure of the encryption key writing device 11. As illustrated in FIG. 6, the encryption key writing device 11 includes a data communication unit 110, an encryption key storage 111, an encryption key transmitting unit 112, an ID receiving unit 113, an ID transmitting unit 114, and an authentication unit 115.

The data communication unit 110 transmits and receives data to and from the sensor tag 2, The encryption key storage 111 stores the encryption key set by the administrator of the encryption key writing device 11.

The encryption key transmitting unit 112 reads the encryption key stored in the encryption key storage 111, and transmits the encryption key to the sensor tag 2 through the data communication unit 110.

The ID receiving unit 113 receives an ID data input from outside of the encryption key writing device 11, and outputs the received ID data to the ID transmitting unit 114.

The ID transmitting unit 114 transmits the ID data output from the ID receiving unit 113 to the sensor tag 2 through the data communication unit 110.

The authentication unit 115 performs an authentication process for authenticating the validity of the encryption key writing device 11 for the sensor tag 2 using the data for authentication stored inside.

3. Measured Data Reading Device 13

Figure 7:
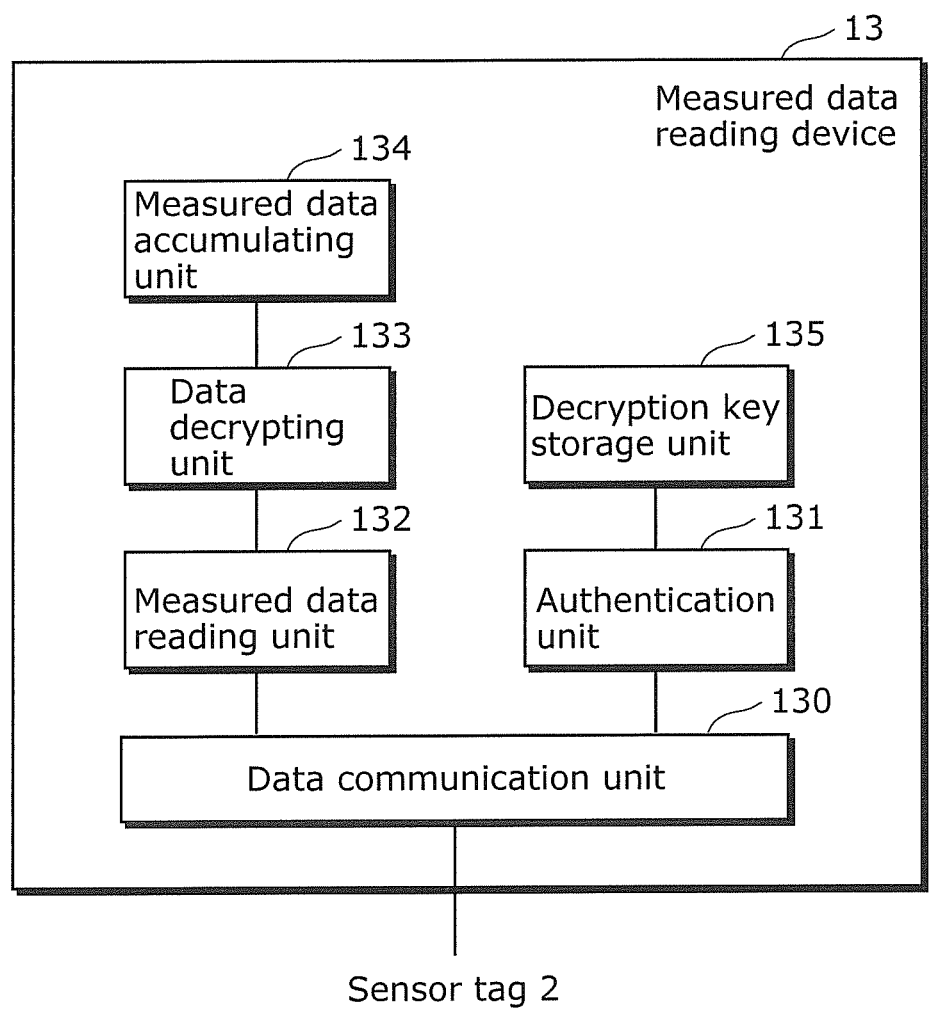
FIG. 7 is a block diagram illustrating the structure of a measured data reading device according to the first and second embodiments of the present invention.

FIG. 7 is a block diagram illustrating the structure of the measured data reading device 13. As illustrated in FIG. 7, the measured data reading device 13 includes a data communication unit 130, an authentication unit 131, a decryption key storage unit 135, a measured data reading unit 132, a data decrypting unit 133, and a measured data accumulating unit 134.

The data communication unit 130 transmits and receives data to and from the sensor tag 2.

The authentication unit 131 performs an authentication process for authenticating the validity of the measured data reading device 13 for the sensor tag 2.

The decryption key storage unit 135 stores the decryption key set by the administrator of the measured data reading device 13.

The measured data reading unit 132 receives the encrypted measurement data from the sensor tag 2 and outputs the encrypted measurement data to the data decrypting unit 133.

The data decrypting unit 133 decrypts, using the decryption key read from the decryption key storage unit 135, the encrypted measurement data received from the measured data reading unit 132, and calculates the measured data in plaintext. The data decrypting unit 133 outputs the calculated measurement data in plaintext to the measured data accumulating unit 134.

The measured data accumulating unit 134 stores the measured data in plaintext received from the data decrypting unit 133.

<Operation>

The following describes the process performed by the sensor tag 2 with reference to the drawings.

Figure 8:
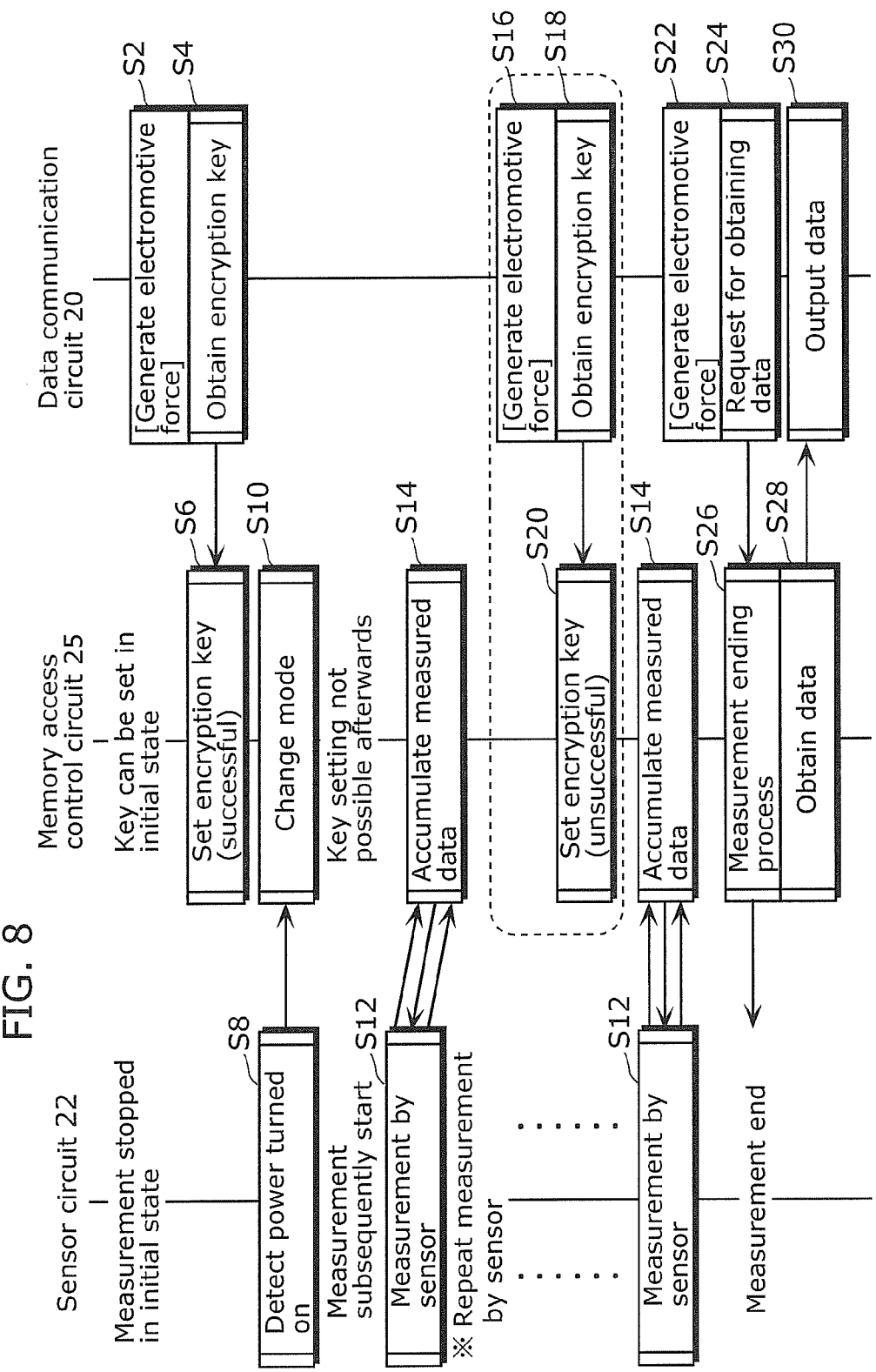
FIG. 8 is a flowchart illustrating the entire operations of the sensor tag according to the first and second embodiments.

FIG. 8 is a flowchart illustrating the entire operations of the sensor tag 2. In FIG. 8, process flow between the sensor circuit 22, the memory access control circuit 25, and the data communication circuit 20 is illustrated.

The process performed by the sensor tag 2 is roughly classified into three processes: the key setting process 3, the measuring process 4, and the measured data reading process 5.

First, the key setting process 3 is performed. More specifically, the data communication unit 110 in the encryption key writing device 11 transmits an activation signal to the antenna 21 in the sensor tag 2. The antenna 21 outputs the received activation signal to the electromotive force generating circuit 30. The electromotive force generating circuit 30 generates electromotive force from the activation signal, and operates the circuits in the sensor tag 2, including the data communication circuit 20 (S2). The following operations by the data communication circuit 20 is performed using the electromotive force generated by the activation signal appropriately received form the data communication unit 110 in the encryption key writing device 11.

The data communication circuit 20 obtains the encryption key from the encryption key writing device 11 (S4).

The memory access control circuit 25 sets the obtained encryption key to the memory 24 (S6).

With the process described above, the encryption key is set on the memory 24. Note that the process in S4 and S6 shall be described later in detail.

Subsequently, the insulator 27 is removed form the sensor tag 2, starting the measuring process 4. More specifically, the power source 23 is switched on, and the power source status detecting unit 225 detects that the power source 23 is on (S8). When it is detected that the power source 23 is on, the memory access control circuit 25 changes the memory access control rule (mode) (S10). More specifically, writing the encryption key and ID from the data communication circuit 20 into the memory 24 is prohibited. The mode change disables the update of the encryption key afterwards (S16, S18, and S20). This prevents the encryption key to be inadvertently rewritten when encrypting the measured data.

When the power source 23 is on, the sensor circuit 22 measures the biological information of the person to be measured 12, and outputs the measured data to the memory access control circuit 25 (S12). The memory access control circuit 25 accumulates the output measured data on the memory 24 (S14). Subsequently, the process in S12 and S14 is repeatedly performed. Note that the process in S8 to S14 shall be described later in detail.

Next, the measured data reading process 5 is performed. First, the data communication unit 130 in the measured data reading device 13 transmits an activation signal to the antenna 21 in the sensor tag 2. The antenna 21 outputs the received activation signal to the electromotive force generating circuit 30. The electromotive force generating circuit 30 generates electromotive force from the activation signal, and operates the circuits in the sensor tag 2, including the data communication circuit 20 (S22). The following operations by the data communication circuit 20 is performed by the operation using the electromotive force generated by the activation signal appropriately received form the data communication unit 130 in the measured data reading device 13.

The data communication circuit 20 outputs a request signal for obtaining the measured data to the memory access control circuit 25, based on a request for obtaining the measured data from the is measured data reading device 13 (S24). The memory access control circuit 25 responds the request signal for obtaining the measured data, and stops the measurement of the biological information by the sensor circuit 22 (S26). Subsequently, the memory access control circuit 25 reads the measured data accumulated in the memory 24, and outputs the measured data to the data communication circuit 20 (S28). The data communication circuit 20 receives the measured data from the memory access control circuit 25, and outputs the measured data to the measured data reading device 13 (S30). Note that the process in S24 to S30 shall be described later in detail.

1. Key Setting Process 3 (S4, S6)

The following describes the detail of the key setting process 3. As illustrated on the left side of FIG. 1, the key setting process 3 is a process for setting the encryption key on the sensor tag 2 with the encryption key not set, performed by the encryption key writing device 11. Typically, the encryption key writing device 11 is owned and managed by the hospital, and key setting process 3 is performed when the sensor tag 2 with the encryption key not set, is purchased by the hospital.

<Data Setting and Other Processes>

In the encryption key writing device 11 in FIG. 6, the encryption key storage 111 stores the encryption key set in advance by the administrator of the encryption key writing device 11. The authentication unit 115 stores password data in a predetermined digit. Furthermore, the authentication unit 201 in the data communication circuit 20 in the sensor tag 2 stores a hash value which is a result of a hash function to the password data as data for validating the authentication.

The memory access control rule that allows the following memory accesses only, and that denies other memory accesses is set on the memory access control circuit 25 in the sensor tag 2.

(1) Writing the Encryption Key from the Data Communication Circuit 20
(2) Writing the ID from the Data Communication Circuit 20
(3) Reading the Encrypted Measurement Data from the Data Communication Circuit 20
(4) Reading the Encryption Key from the Sensor Circuit 22
(5) Writing the Encrypted Measurement Data from the Sensor Circuit At the time of key setting process 3, the sensor tag 2 illustrated in FIG. 3 is attached with the insulator 27. Thus, the sensor circuit 22 does not receive the power supply from the power source 23, and does not operate.

<Encryption Key Obtaining Process (S4)>

Figure 9:
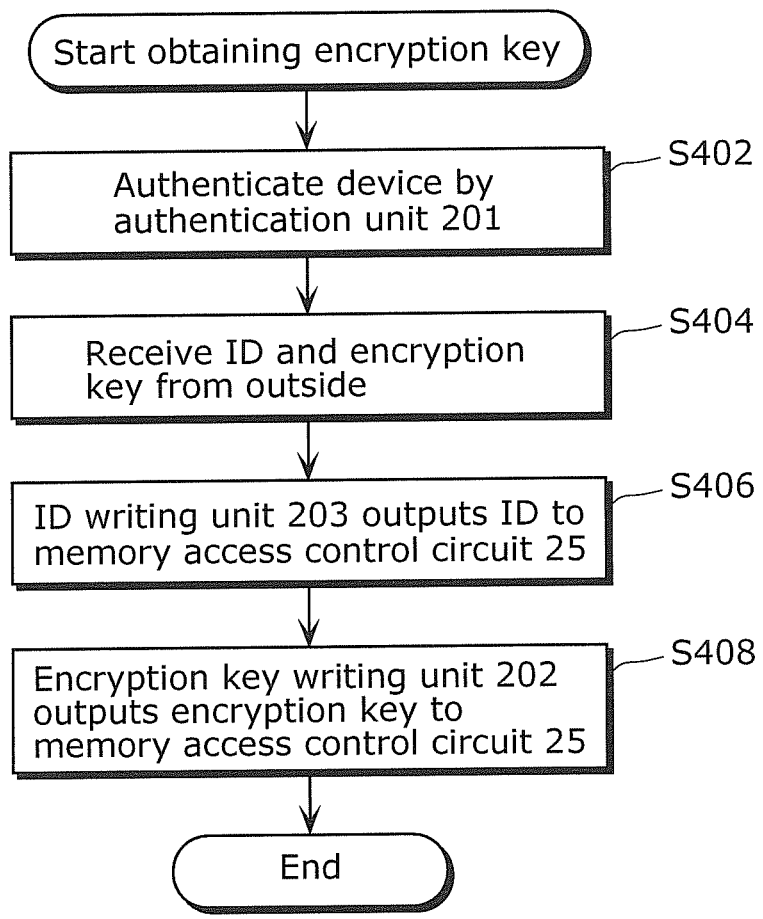
FIG. 9 is a flowchart illustrating an encryption key obtaining process according to the first and second embodiments in detail.

FIG. 9 is a flowchart illustrating the encryption key obtaining process (S4) in detail.

The authentication unit 115 in the encryption key writing device 11 transmits the password data which is the stored authentication data to the sensor tag 2 through the data communication unit 110. The antenna 21 in the sensor tag 2 receives the authentication data, and transfers the authentication data to the authentication unit 201 through the data communication unit 200 in the data communication circuit 20. The authentication unit 201 calculates the hash value which is a result of the calculation of the hash function on the received authentication data. The authentication unit 201 compares the calculated hash value and the data for verifying authentication stored in the authentication unit 201, verifies the encryption key writing device 11 as valid when the values match, and allows the subsequent key setting process. When the values do not match, it is determined that the encryption key writing device 11 is not valid, and the subsequent key setting process is stopped (S402).

The operator of the encryption key writing device 11 inputs, to the encryption key writing device 11, the ID that the operator would like to set on the sensor tag 2. The input ID is received by the ID receiving unit 113, and transferred to the data communication unit 110 through the ID transmitting unit 114. At the same time, the encryption key transmitting unit 112 reads the encryption key stored in the encryption key storage 111, and transfers the encryption key to the data communication unit 110. The data communication unit 110 transmits the ID and the encryption key to the sensor tag 2. The antenna 21 in the sensor tag 2 receives the ID and the encryption key transmitted from the encryption key writing device 11. The antenna 21 transfers the received ID and the encryption key to the data communication unit 200 in the data communication circuit 20. The data communication unit 200 transfers the ID to the ID writing unit 203, and transfers the encryption key to the encryption key writing unit 202 (S404).

The ID writing unit 203 transfers the received ID to the memory access control circuit 25 (S406).

The encryption key writing unit 202 transfers the received encryption key to the memory access control circuit 25 (S408).

<Encryption Key Setting Process (S6)>

The following describes the encryption key setting process (S6).

Figure 10:
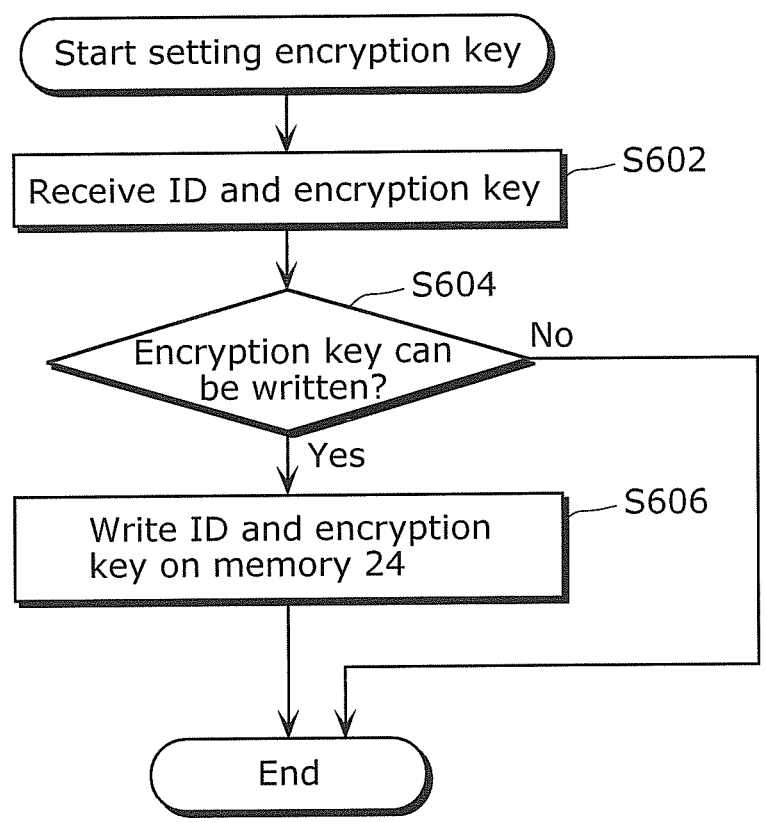
FIG. 10 is a flowchart illustrating an encryption key setting process according to the first and second embodiments in detail.

FIG. 10 is a flowchart illustrating the encryption key setting process (S6) in detail.

The memory access control circuit 25 receives an ID from the ID writing unit 203, and receives the encryption key from the encryption key writing unit 202 (S602).

The memory access control circuit 25 checks the memory access checking rule that is set inside, and confirms that the data communication circuit 20 is allowed to write the ID and the encryption key (Yes in S604), writes the ID on the ID storage region in the memory 24, and writes the encryption key on the encryption key storage region on the memory 24 (S606).

The key setting process 3 is completed with the series of process described above (S4, S6).

2. Measuring Process 4 (S8 to S14)

The following describes the detail of the measuring process 4. As illustrated in the middle of FIG. 1, the measuring process 4 is a process for regularly measuring the biological information of the person to be measured 12 by the sensor tag 2 with the encryption key set. Typically, the measuring process 4 is performed when measuring the biological information of the person to be measured 12 who is a patient provided with the sensor tag 2 with the encryption key set from the hospital. The person to be measured to be measured 12 is so at home, for example, and attaches the sensor tag 2 on his body.

<Power on Detecting Process (S8)>

Figure 11:
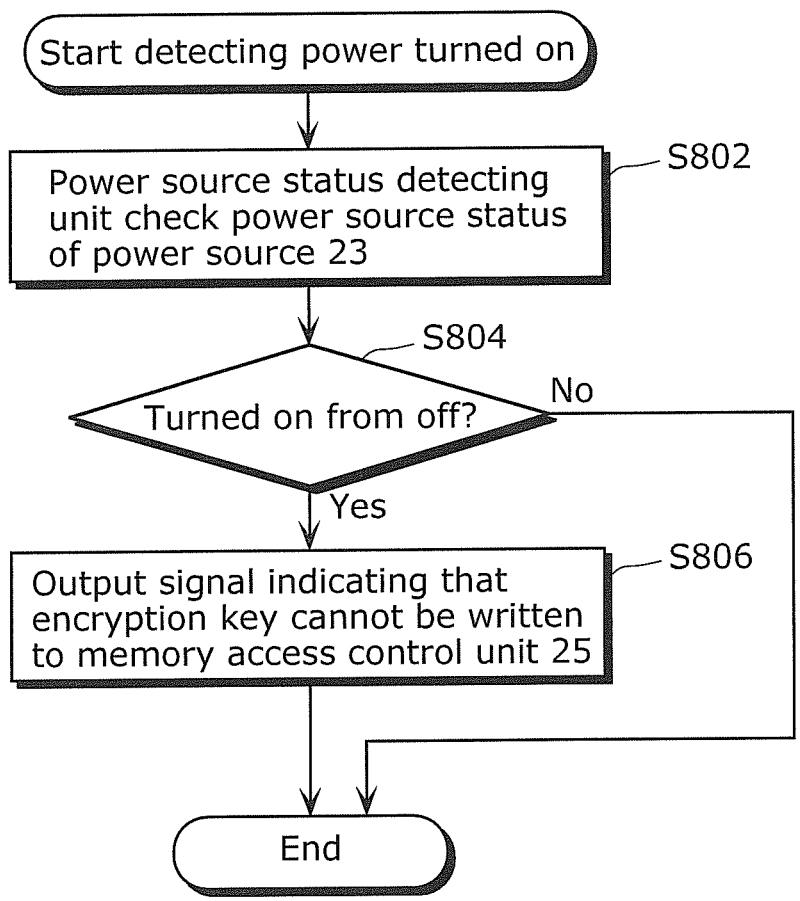
FIG. 11 is a flowchart illustrating a power on detection process according to the first embodiment of the present invention in detail

FIG. 11 is a flowchart illustrating the power on detecting process (S8) in detail.

The power source status detecting unit 225 checks the status of power supply from the power source 23 (S802). The person to be measured 12 removes the insulator 27 from the sensor tag 2 when starting the measurement. With this, the power supply from the power source 23 to the sensor circuit 22 starts and the sensor circuit 22 starts to operate. From now on, the sensor circuit 22 performs processes with the power supplied from the power source 23.

When it is confirmed that the power supply from the power source 23 is turned on from off (Yes in S804), the power source status detecting unit 225 outputs a signal indicating that the encryption key cannot be written to the memory access control circuit 25, to instruct the memory access control circuit 25 from prohibiting the data communication circuit 20 from writing the encryption key and the ID into the memory 24 (S806).

<Mode Changing Process (S10)>

Figure 12:
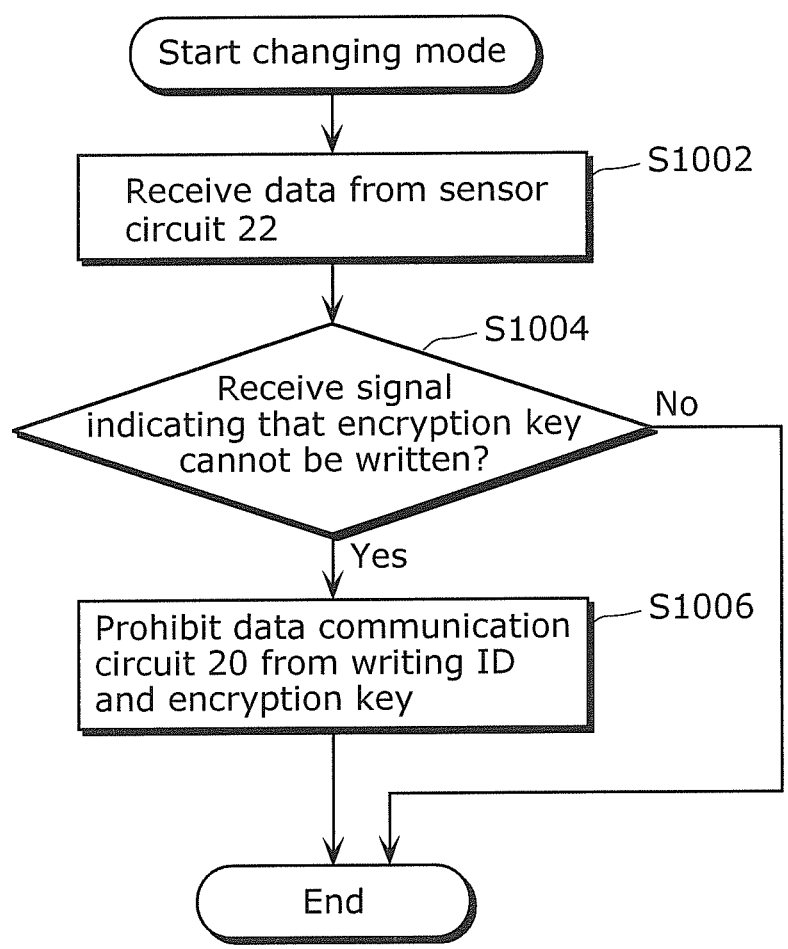
FIG. 12 is a flowchart illustrating a mode change process according to the first embodiment of the present invention in detail.

FIG. 12 is a flowchart illustrating the mode changing process (S10) in detail.

The memory access control circuit 25 receives the data from the sensor circuit 22 (S1002). When the data received from the memory access control circuit 25 is the signal indicating that the encryption key cannot be written (Yes in S1004), the memory access control rule updating unit 26 changes the memory access control rule (mode) to prohibit the data communication circuit 20 from writing the encryption key and the ID into the memory 24 (S1006). More specifically, the memory access control rule updating unit 26 updates the memory access control rule set in the memory access control circuit 25 to allow the following memory accesses and to deny the other memory accesses.

(3) Reading the Encrypted Measurement Data from the Data Communication Circuit 20
(4) Reading the Encryption Key from the Sensor Circuit 22
(5) Writing the Encrypted Measurement Data from the Sensor Circuit As described above, due to the update on the memory access control rule, the encryption key cannot be updated afterwards (S16, S18, S20 in FIG. 8).

<Sensor Measuring Process (S12)>

Figure 13:
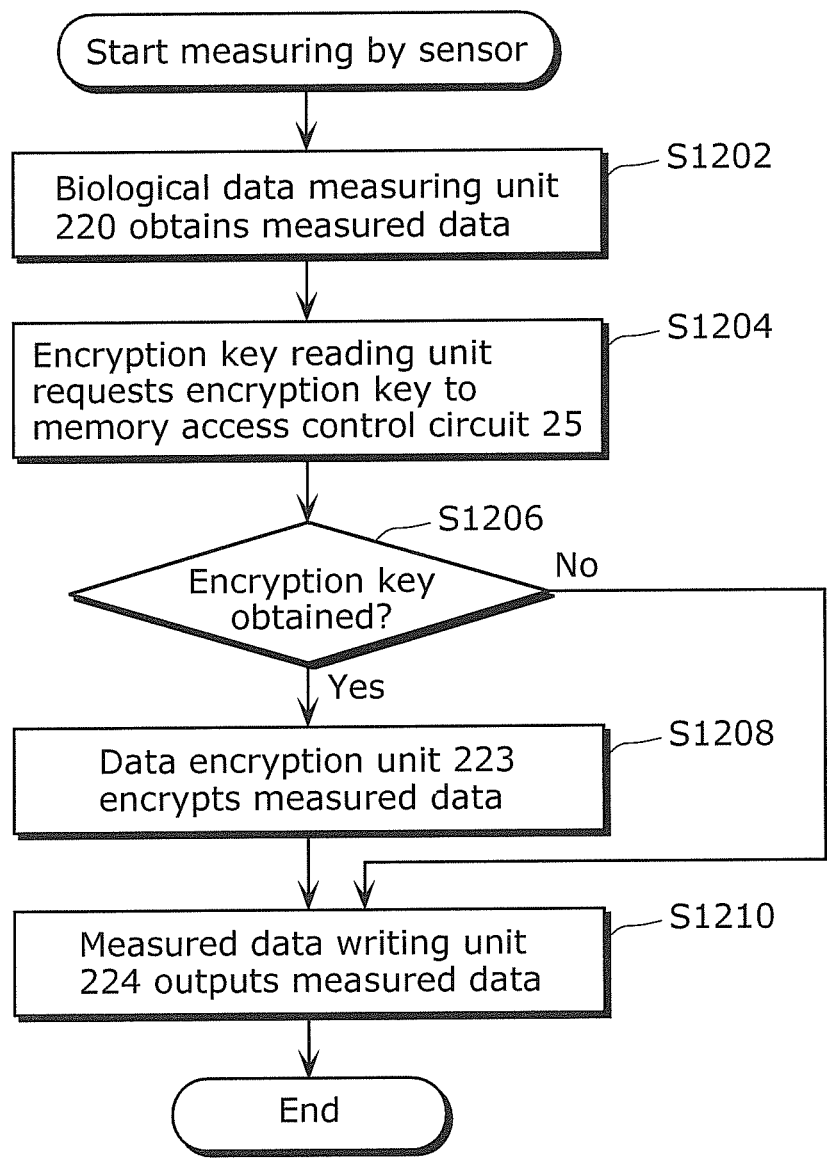
FIG. 13 is a flowchart illustrating a sensor measuring process according to the first embodiment of the present invention in detail.

FIG. 13 is a flowchart illustrating the sensor measuring process (S12) in detail.

The Biological data measuring unit 220 measures the biological information from the person to be measured 12. The measured biological information (hereafter referred to as measured data) with the count value transferred from the timer unit 221 added is transferred to the data encrypting unit 223 (S1202).

The encryption key reading unit 222 requests the encryption key to the memory access control circuit 25 (S1204).

When the encryption key reading unit 222 obtains the encryption key from the memory access control circuit 25 (Yes in S1206), the data encrypting unit 223 receives the encryption key from the encryption key reading unit 222, and encrypts, using the encryption key, the measured data received from the biological data measuring unit 220, and generates the encrypted measurement data (S1208). Note that, although the count value is not encrypted here, the count value may be encrypted.

The data encrypting unit 223 adds the count value received from the biological data measuring unit 220 to the encrypted measurement data, and transfers the data to the measured data writing unit 224. The measured data writing unit 224 transfers the encrypted measurement data and the count value received from the data encrypting unit 223 to the memory access control circuit 25, and sends a request for writing data into the memory 24 (S1210).

When the encryption key reading unit 222 does not receive the encryption key from the memory access control circuit 25 (No in S1206), the data encrypting unit 223 adds the count value received from the biological data measuring unit 220 to the measured data, and transfers the data to the measured data writing unit 224, without encrypting the measured data. The measured data writing unit 224 transfers the unencrypted measurement data and the count value received from the data encrypting unit 223 to the memory access control circuit 25, and sends the request for writing data into the memory 24 (S1210).

<Measured data Accumulating Process (S14)>

Figure 14:
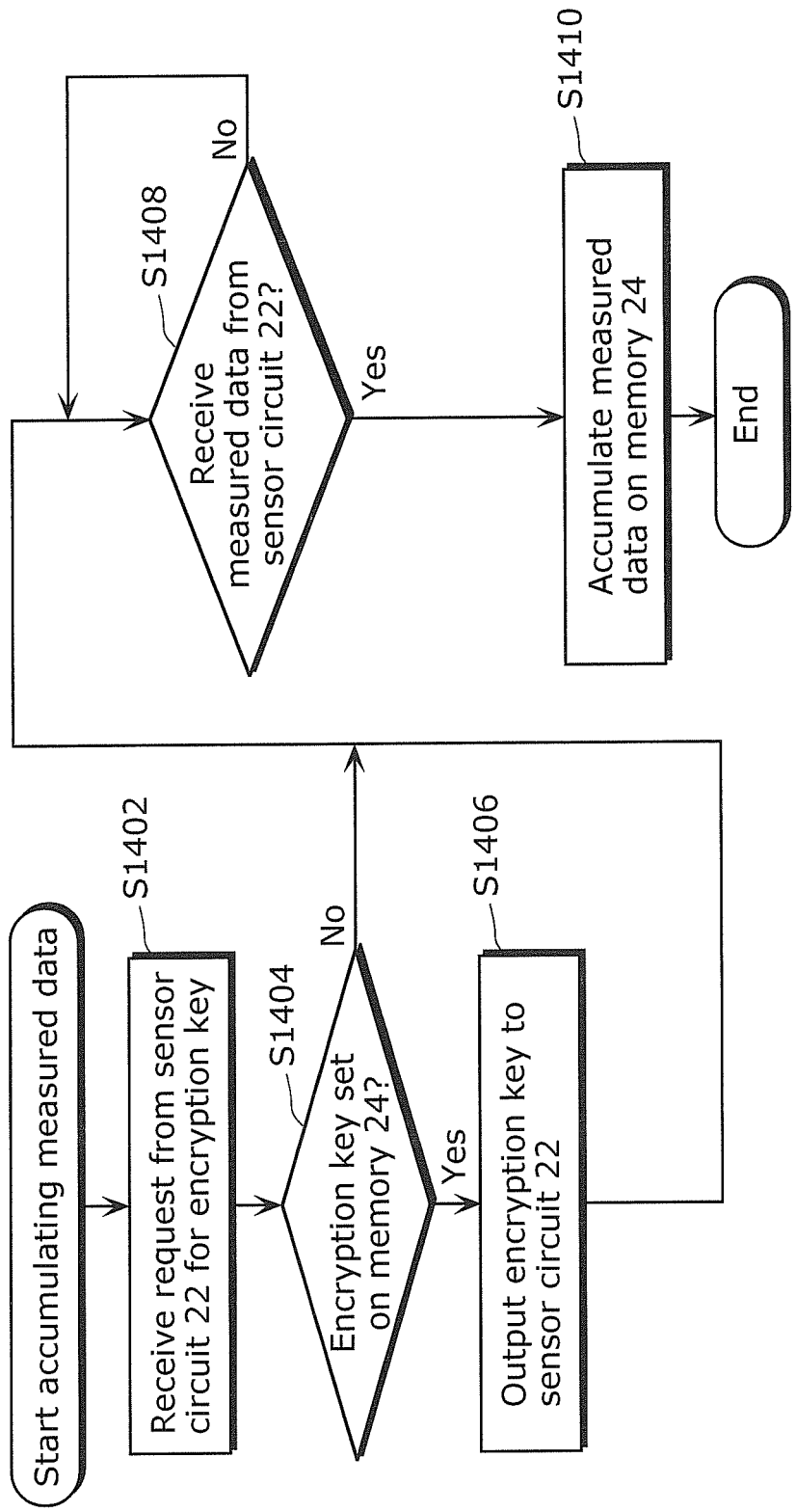
FIG. 14 is a flowchart illustrating a measured data accumulating process according to the first embodiment of the present invention in detail.

FIG. 14 is a flowchart illustrating the measured data accumulating process (S14) in detail.

The memory access control circuit 25 receives a request for the encryption key from the sensor circuit 22 (S1402). The memory access control circuit 25 checks the memory access control rule held in the memory access control circuit 25, and confirms that the sensor circuit 22 is allowed to read the encryption key. When that is confirmed, the memory access control circuit 25 checks whether or not the encryption key is set on the memory 24 (S1404).

If the encryption key is set (Yes in S1404), the memory access control circuit 25 reads the encryption key from the encryption key storage region of the memory 24, and transfers the encryption key to the encryption key reading unit 222 on the sensor circuit 22 (S1406).

The memory access control circuit 25 waits until the encrypted measurement data and the count value are received from the measured data writing unit 224 in the sensor circuit 22 (S1408). When the encrypted measurement data and the count value are received (Yes in S1408), the memory access control circuit 25 checks the memory access control rule held inside, and confirms that the sensor circuit 22 is allowed to write the encrypted measurement data. When that is confirmed, the memory access control circuit 25 writes the encrypted measurement data and the count value received from the measured data writing unit 224 in the sensor circuit 22 to the encrypted measurement data storage region on the memory 24 (S1410). Note that, when the encryption key is not set on the memory 24 (No in S1404), the same process (S1408, S1410) is performed on the unencrypted measurement data.

The series of measuring process 4 (S12, S14) are repeatedly performed.

<Data in Memory 24 after Measuring Process 4>

Figure 15:
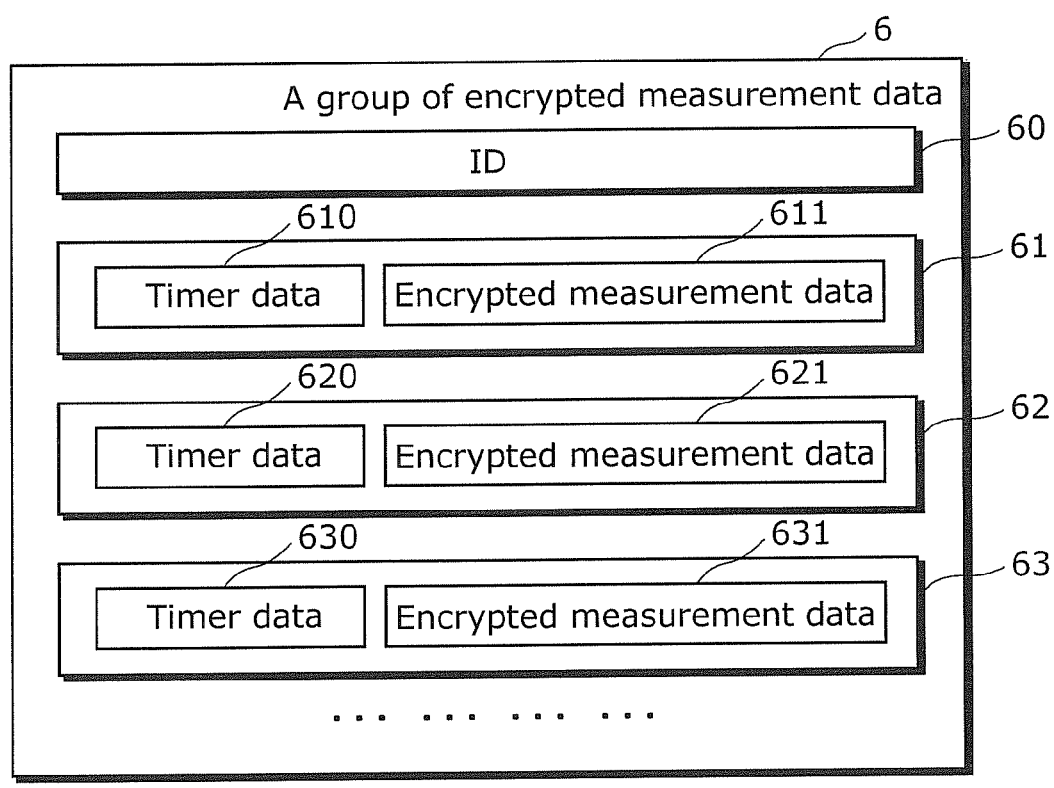
FIG. 15 is a block diagram illustrating the structure of a group of encrypted data according to the first and second embodiments of the present invention.

In the measuring process 4, the biological information of the person to be measured 12 is measured regularly, and sequentially added to the memory 24. After the measuring process 4, the memory 24 stores a group of encrypted measurement data 6 as illustrated in FIG. 15 in addition to the encryption key. The group of encrypted measurement data 6 includes one ID 60 and data sets (a data set 61, 62, 63 . . . ) including one or more set of timer data (timer data 610, 620, 630 . . . ) and encrypted measurement data (encrypted measurement data 661, 621, 631 . . . ). ID 60 is an ID set on the sensor tag 2 with the encryption key in key setting process 3. The sets of timer data and encrypted measurement data are added by one set in the measuring process 4 each time the measured data accumulating process is performed.

3. Measured Data Reading Process 5 (S24 to S30)

The following describes the detail of the measured data reading process 5. As illustrated on the right side of FIG. 1, the measured data reading process 5 is a process for reading, by measured data reading device 13, the encrypted measurement data from the sensor tag 2 after the measuring process. The typical example is performed when reading, using the measured data reading device 13 at the hospital, the encrypted measurement data from the sensor tag 2 after measuring process submitted from the person to be measured 12 who is the patient.

<Data Setting and Other Processes>

In the measured data reading device 13 illustrated in FIG. 7, the decryption key storage unit 135 stores the decryption key which is set by the administrator of the measured data reading device 13 in advance. The decryption key is paired with the encryption key stored in the encryption key storage 111 in the encryption key writing device 11. More specifically, the original data can be obtained by decrypting; using the decryption key, the encrypted data of data encrypted using the encryption key. The authentication unit 131 stores the password data identical to the password data stored in the authentication unit 115 in the encryption key writing device 11.

Furthermore, as described above, the memory 24 in the sensor tag 2 stores the group of encrypted measurement data 6.

<Data Obtaining Request Process (S24)>

Figure 16:
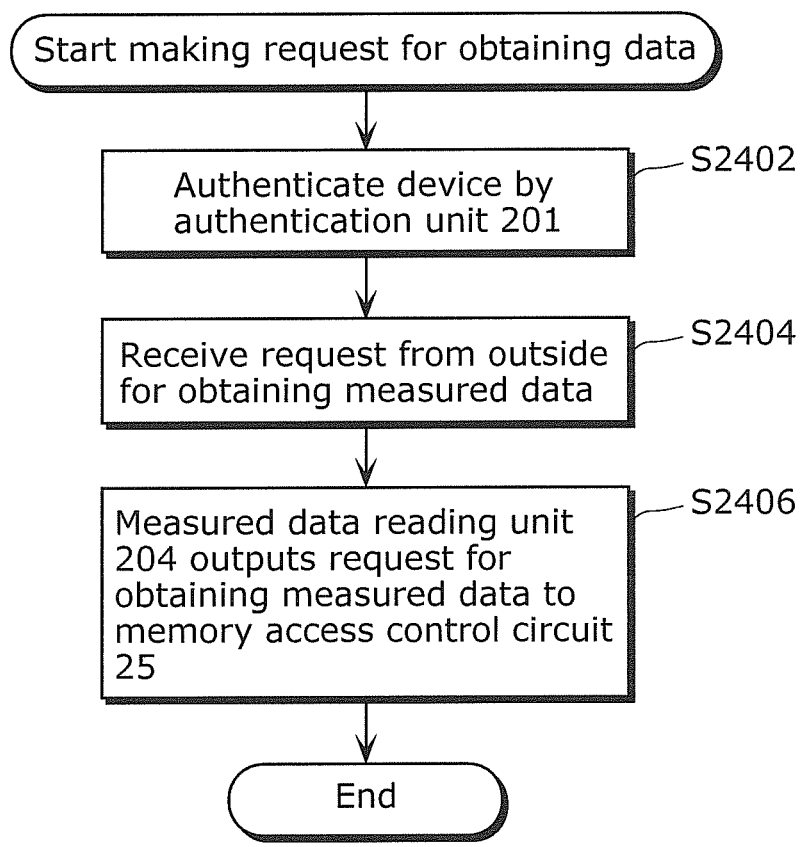
FIG. 16 is a flowchart illustrating a data obtainment requesting process according to the first and second embodiments in detail.

FIG. 16 is a flowchart illustrating the data obtaining request process (S24) in detail.

The authentication unit 131 in the measured data reading device 13 transmits the password data which is the stored authentication data to the sensor tag 2 through the data communication unit 130. The antenna 21 in the sensor tag 2 receives the authentication data, and transfers the authentication data to the authentication unit 201 through the data communication unit 200 in the data communication circuit 20. The authentication unit 201 calculates the hash value which is a result of the calculation of the hash function on the received authentication data. The authentication unit 201 compares the calculated hash value with the data for verifying authentication stored in the authentication unit 201, verifies the measured data reading device 13 as valid when the values match, and allows the subsequent measured data reading process. When the values do not match, the authentication unit 201 determines that the measured data reading device 13 is invalid, and stops the subsequent measured data reading process (S2402).

The measured data reading unit 132 transmits the request signal for obtaining the measured data to the sensor tag 2 through the data communication unit 130. The antenna 21 in the sensor tag 2 receives the request signal for obtaining the measured data transmitted from the measured data reading device 13. The antenna 21 transfers the received request signal for obtaining the measured data to the data communication unit 200 in the data communication circuit 20. Furthermore, the data communication unit 200 transfers the request signal for obtaining the measured data to the measured data reading unit 204 (S2404). The measured data reading unit 204 then transmits the request signal for obtaining the measured data to the memory access control circuit 25 (S2406).

<Measurement Ending Process (S26)>

Figure 17:
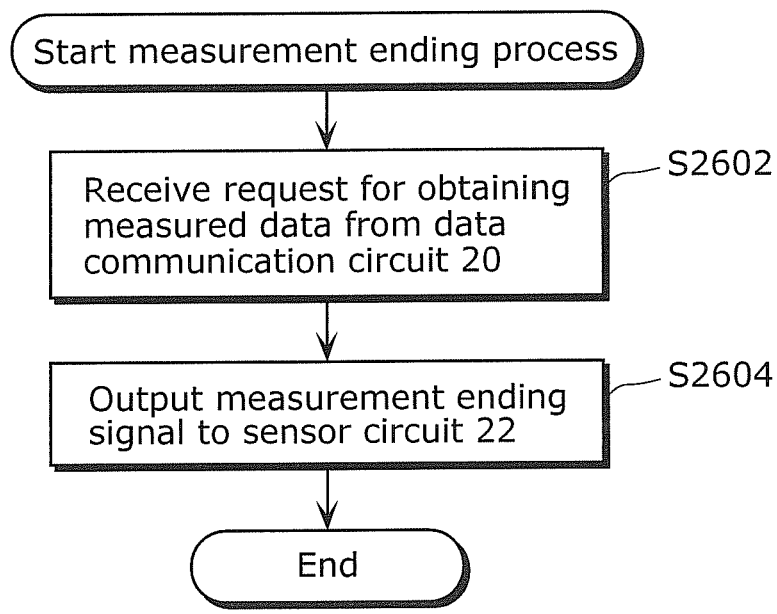
FIG. 17 is a flowchart illustrating a measurement ending process according to the first and second embodiments in detail.

FIG. 17 is a flowchart illustrating the measurement ending process (S26) in detail.

When the request signal for obtaining the measured data is received from the measured data reading unit 204 in the data communication circuit 20 (S2602), the memory access control circuit 25 outputs the measurement ending signal to the sensor circuit 22 (S2604). At the same time, the memory access control rule updating unit 26 changes the memory access control rule (mode) set inside the memory access control circuit 25 to prohibit the sensor circuit 22 from writing the encrypted measurement data into the memory 24. With this, the encrypted measurement data is not written on the memory 24 by the sensor circuit 22 when the data communication circuit 20 is transmitting the encrypted measurement data. Thus, it is possible to prevent the encrypted measurement data stored in the memory 24 from being left without transmission.

The sensor circuit 22 that receives the measurement ending signal ends the measurement of the biological information after that. Note that, the memory access control circuit 25 may stop storing the encrypted measurement data on the memory 24, instead of the sensor circuit 22 ending the measurement.

<Data Obtaining Process (S28)>

Figure 18:
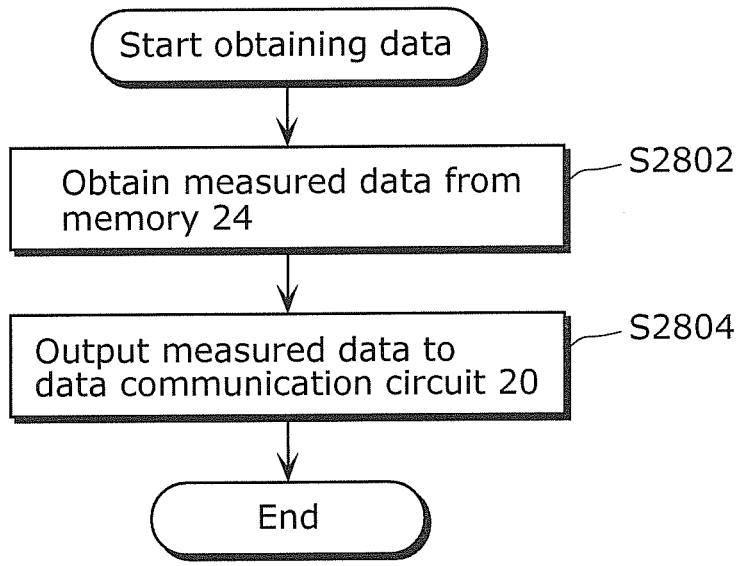
FIG. 18 is a flowchart illustrating data obtaining process according to the first and second embodiments in detail.

FIG. 18 is a flowchart illustrating the data obtaining process (S28) in detail.

The memory access control circuit 25 checks the memory access control rule set inside, and confirms that the data communication circuit 20 is allowed to read the encrypted measurement data. When it is confirmed, the memory access control circuit 25 reads the group of encrypted measurement data 6 from the memory 24 (S2802), and transfers the read data to the measured data reading unit 204 (S2804).

<Data Outputting Process (S30)>

Figure 19:
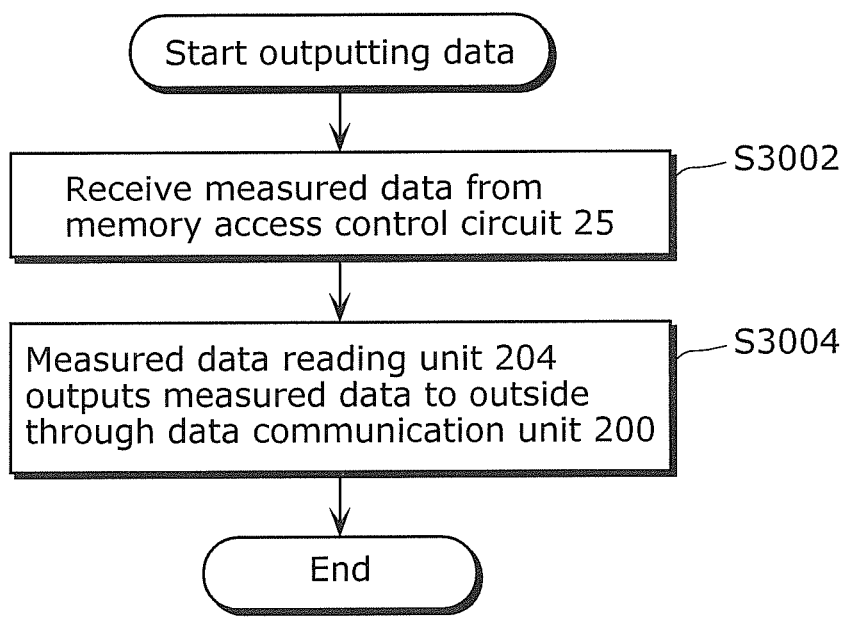
FIG. 19 is a flowchart illustrating data output process according to the first and second embodiments in detail.

FIG. 19 is a flowchart illustrating the data outputting process (S30) in detail.

The measured data reading unit 204 receives the group of encrypted measurement data 6 transferred from the memory access control circuit 25 (S3002). The measured data reading unit 204 transmits the received group of encrypted measurement data 6 to the measured data reading device 13 through the data communication unit 200 and the antenna 21 (S3004).

The group of encrypted measurement data 6 is transferred to the data decrypting unit 133 through the data communication unit 130, the measured data reading unit 132 in the measured data reading device 13. The data decrypting unit 133 decrypts, using the decryption key read from the decryption key storage unit 135, the encrypted measurement data 611, 621, and 631 in the received group of encrypted measurement data 6, and obtains the measured data in plaintext. Subsequently, the data decrypting unit 133 transfers the data obtained by replacing the encrypted measurement data 611, 621, and 631 with the measured data in plaintext to the measured data accumulating unit 134 as a group of measured data.

The measured data accumulating unit 134 stores the received group of measured data in plaintext.

The measured data reading process 5 is completed with the series of process (S24 to S30).

The measured data accumulating unit 134 stores a group of measured data including one ID and at least one set of timer data and plaintext measured data. The ID to be set may be determined according to the operation form determined by the administrator who manages the encryption key writing device 11 and the measured data reading device 13. For example, the ID may be a sensor tag ID for identifying the sensor tag, or may be an ID for person to be measured in order to identify the patient to be handed with the sensor tag (person to be measured). The ID set differs for each sensor tag in the case of operation according to the former rule. In the case of operation according to the latter rule, identical ID (patient ID) is set for all the sensor tag to be handed to a patient. The timer data which is paired with the measured data is used as the time information indicating the time when the measured data is measured.

The group of measured data stored in the measured data accumulating unit 134 is read as necessary, and used for health management and medical checkup for the person to be measured 12 who is the patient.

Figure 20:
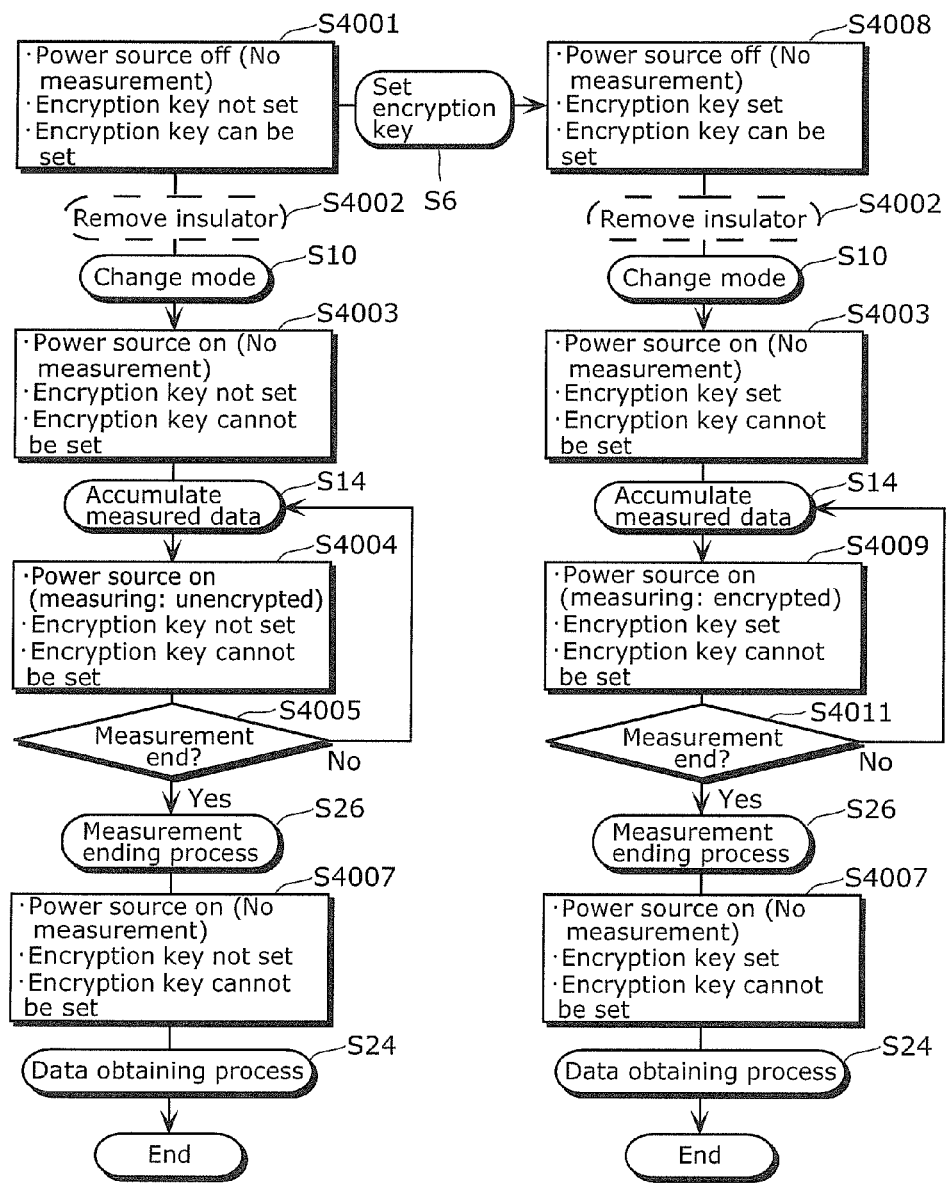
FIG. 20 illustrates the transition of memory access control rule (mode) held by a memory access control circuit 25 according to the first embodiment of the present invention.

FIG. 20 illustrates the transition of the memory access control rule (mode) held by the memory access control circuit 25.

In the initial state (S4001), the power supply from the power source 23 is off, and no measurement is performed. Furthermore, no encryption key is set on the memory 24, and according to the memory access control rule, the data communication circuit 20 is allowed to write the encryption key.

When the insulator 27 is removed from the sensor tag 2 in this state (S4002), the mode changing process (S10) is performed, and the state transitions to the next state (S4003). In this state (S4003), the power supply from the power source 23 is on. However, no measurement is performed. Furthermore, no encryption is set on the memory 24 yet. The memory access control rule prohibits the data communication circuit 20 from writing the encryption key.

When the sensor measuring process (S12) and the measured data accumulating process (S14) are started in this state, the state transitions to the state in which unencrypted measured is accumulated (S4004), and the state is maintained until the measuring process ends. When the measuring process ends (Yes in S4005), the measurement ending process (S26) is executed, and the state transitions to the state where the measurement of the biological information stops (S4007). The obtaining process (S24) is executed afterwards, and the series of process end.

When the encryption key setting process (S6) is performed in the initial state (S4001), the state transitions to the state in which the encryption key is set (S4008).

When the insulator 27 is removed from the sensor tag 2 in this state (S4002), the mode changing process (S10) is performed, and the state transitions to the next state (S4003). In this state (S4003), the power supply from the power source 23 is on. However, no measurement is performed. Furthermore, no encryption is set on the memory 24 yet. The memory access control rule prohibits the data communication circuit 20 from writing the encryption key.

When the sensor measuring process (S12) and the measured data accumulating process (S14) are started in this state, the state transitions to the state in which encrypted measured data is accumulated (S4009), and the state is maintained until the measuring process ends. When the measuring process ends (Yes in S4011), the measurement ending process (S26) is executed, and the state transitions to the state where the measurement of the biological information stops (S4007). The obtaining process (S24) is executed afterwards, and the series of process end.

<Conclusion>

As described above, in the sensor tag 2 according to the embodiment, the data communication circuit that sets the encryption key operates by the power generated from the activation signal received from the encryption key writing device 11. Thus, it is not necessary to remove the insulator 27 and receive the power supply from the embedded power source 23 when setting the encryption key. With this, it is not necessary to turn the power supply from the embedded battery from off to on when setting the encryption key, even when the tag is a small sensor tag in which a switch mechanism capable of freely switching the power supply from the power source 23 between on and off cannot be embedded. Thus, the problem described above; that is, the problem on the wasted battery before starting the measurement does not occur.

Furthermore, it is possible to receive the encryption key wirelessly. Thus, the encryption key on the sensor tag can be set without breaking the sterilized package. Therefore, the sensor tag 2 can be stored in sanitary condition immediately before the use of the sensor tag 2.

Furthermore, once the power is supplied from the power source 23 to the sensor circuit 22, the memory access control rule updating unit 26 updates the memory access control rule in the memory access control circuit 25 so that the encryption key cannot be written. With this, the power is supplied from the power source 23 to the sensor circuit 22, preventing erroneous operations such as inadvertently rewriting the encryption key after the measurement starts.

Variation 1 of First Embodiment

The following measurement ending process (S26) may be performed, instead of the measurement ending process (S26) in the first embodiment illustrated in FIG. 17.

Figure 21:
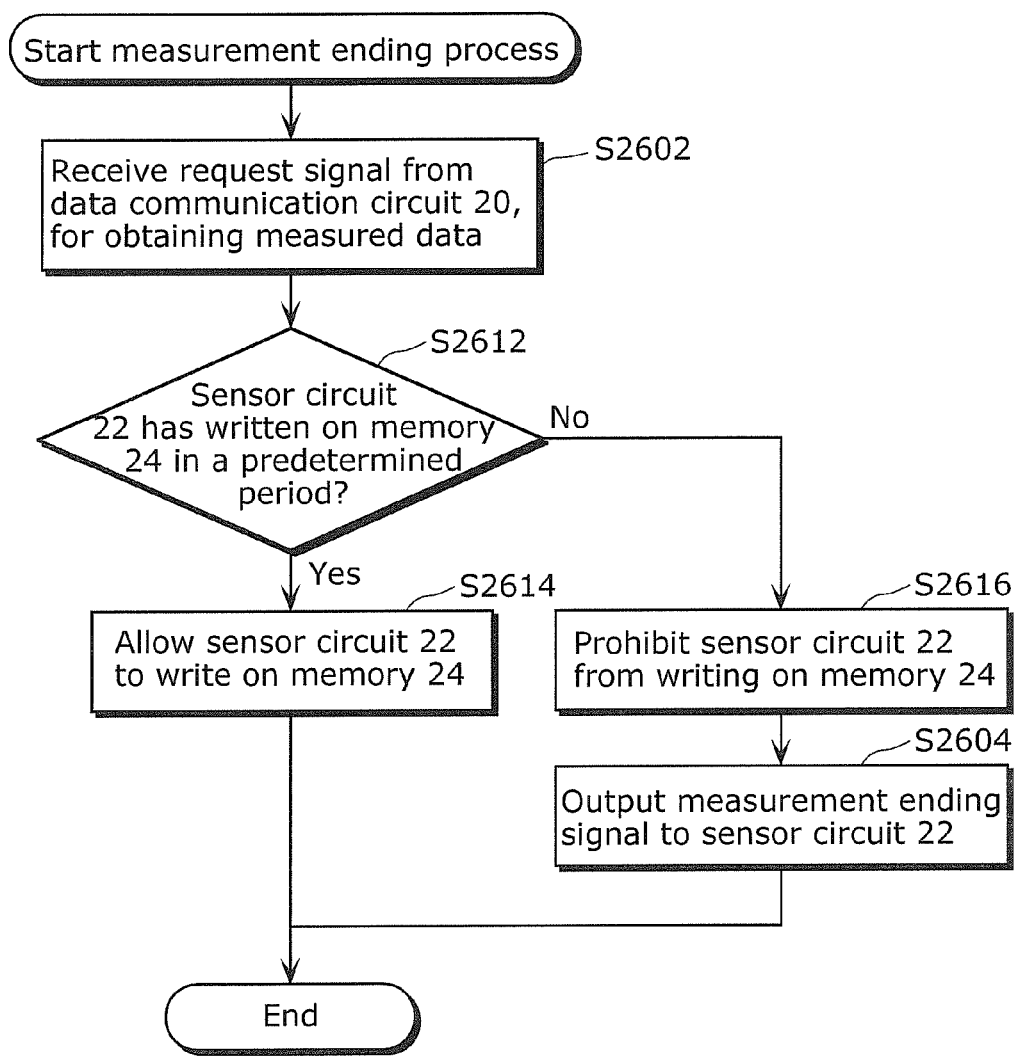
FIG. 21 is a flowchart illustrating a measurement ending process according to the variation 1 of the first embodiment in detail.

FIG. 21 is a flowchart illustrating the measurement ending process (S26) according to variation 1 of the first embodiment.

When the memory access control circuit 25 receives the request signal for obtaining the measured data from the measured data reading unit 204 in the data communication circuit 20 (S2602), the memory access control circuit 25 determines whether or not the sensor circuit 22 has written the encrypted measurement data into the memory 24 within a predetermined period in the past, using the present as a reference (S2612).

When it is determined that the sensor circuit 22 has written the encrypted measurement data into the memory 24 within the predetermined period (Yes in S2612), the memory access control rule updating unit 26 changes the memory access control rule (mode) set inside the memory access control circuit 25 to allow the sensor circuit 22 to write the encrypted measurement data into the memory 24 (S2614).

When it is determined that the sensor circuit 22 has not written the encrypted measurement data into the memory 24 in a predetermined period (No in S2612), the memory access control rule updating unit 26 changes the memory access control rule (mode) set inside the memory access control circuit 25 to prohibit the sensor circuit 22 from writing the encrypted measurement data into the memory 24 (S2616).

After the process in S2616, the memory access control circuit 25 outputs the measurement ending signal to the sensor circuit 22 (S2604).

As described above, according to the variation, when the sensor circuit 22 has not written data into the memory 24 in a predetermined period, the memory access control circuit 25 considers that the power of the power source 23 is used, and prohibits the sensor circuit 22 from writing data into the memory 24. With this, when the memory 24 stores sufficient encrypted measurement data to be sent to the data communication circuit 20, the data communication circuit 20 can read the encrypted measurement data from the memory 24 and can transmit the encrypted measurement data to a predetermined destination. Thus, the inefficient operation in which the encrypted measurement data is transmitted from the memory 24 with the encrypted measurement data sufficient enough for transmitting to the data communication circuit 20 not stored in the memory 24, for example, when the obtaining request by the data communication circuit 20 is received immediately after the power supply from the power source 23 is turned on can be prevented with a simple structure.

Furthermore, when the encryption circuit has written the memory 24 in a predetermined period, the memory access control circuit 25 determines that the power source 23 has some power left, and allows the sensor circuit 22 to write the data into the memory 24, and maintains the prohibition on the data communication circuit 20 from writing the data into the memory 24. With this, when it is determined that the power of the power source 23 is left, even when the request for obtaining the encrypted measurement data stored in the memory 24 is received from the data communication circuit 20, the process for storing, into the memory 24, the encrypted measurement data that should be transmitted to the data communication circuit 20 continues. Thus, the inefficient operation in which the encrypted measurement data is transmitted from the memory 24 with the encrypted measurement data sufficient enough for transmitting to the data communication circuit 20 not stored in the memory 24, for example, when the obtaining request by the data communication circuit 20 is received immediately after the power supply from the power source 23 is turned on can be prevented with a simple structure.

Variation 2 of First Embodiment

The following measurement ending process (S26) may be performed, instead of the measurement ending process (S26) in the first embodiment illustrated in FIG. 17.

Figure 22:
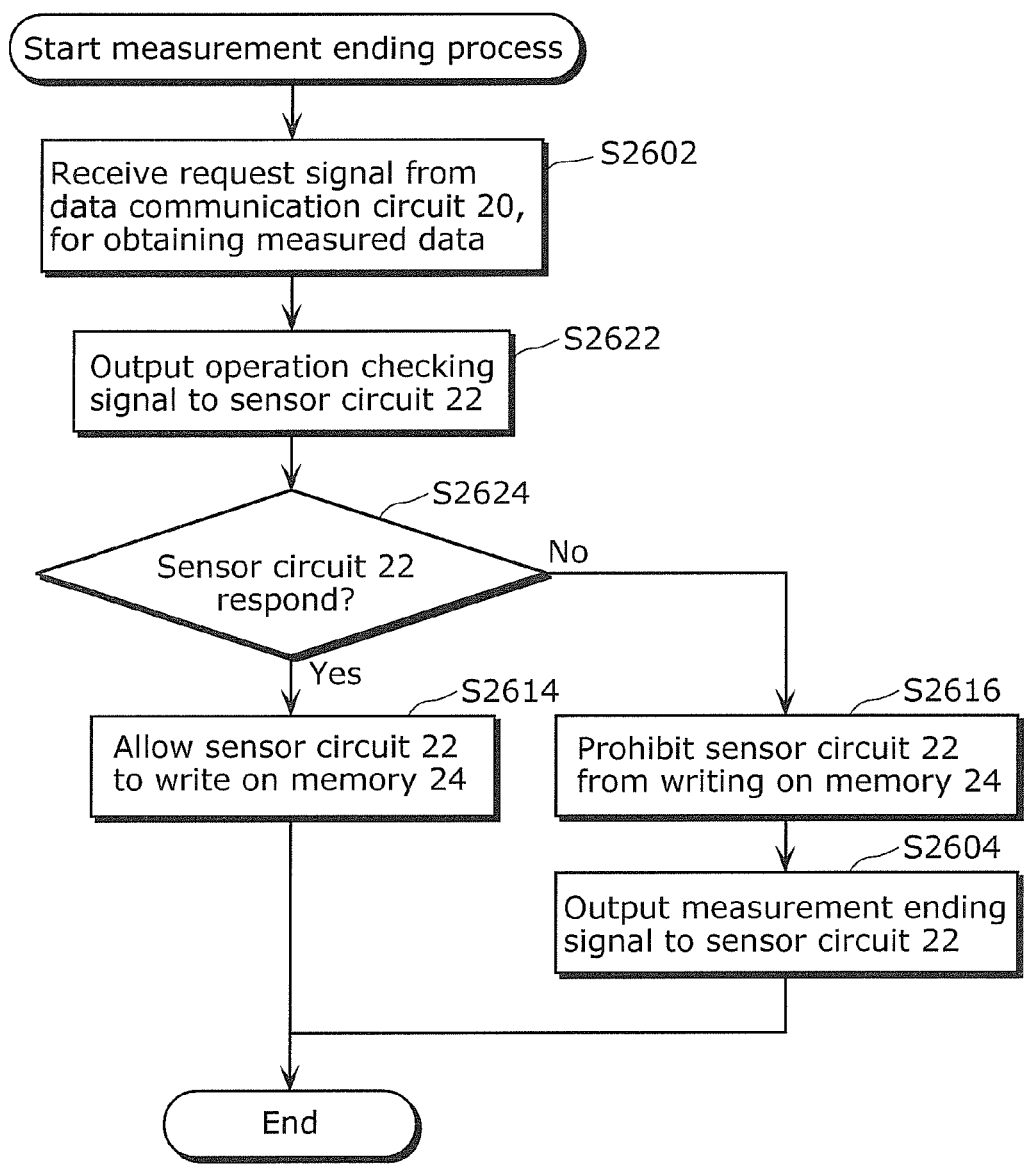
FIG. 22 is a flowchart illustrating a measurement ending process according to the variation 2 of the first embodiment in detail.

FIG. 22 is a flowchart illustrating the measurement ending process (S26) according to the variation 2 of the first embodiment.

When the memory access control circuit 25 receives, from the measured data reading unit 204 in the data communication circuit 20, the request signal for obtaining the measured data in the data communication circuit 20 (S2602), the memory access control circuit 25 outputs the operation checking signal for checking whether or not the sensor circuit 22 is in operation (S2622). When the operation checking signal is received, the sensor circuit 22 in operation outputs a response signal to the memory access control circuit 25.

The memory access control circuit 25 determines whether or not the response signal from the sensor circuit 22 has received within a predetermined period (S2624).

When the operation checking signal is received (Yes in S2624), the memory access control rule updating unit 26 changes the memory access control rule set inside the memory access control circuit 25 to allow the sensor circuit 22 to write the encrypted measurement data into the memory 24 (S2614).

When the operation checking signal is not received (No in S2624), the memory access control rule updating unit 26 changes the memory access control rule (mode) set inside the memory access control circuit 25 to prohibit the sensor circuit 22 from writing the encrypted measurement data into the memory 24 (S2616).

After the process in S2616, the memory access control circuit 25 outputs the measurement ending signal to the sensor circuit 22 (S2604).

As described above, according to this variation, the memory access control circuit 25 considers that the power of the power source 23 has run out when there is no response from the sensor circuit 22 within a predetermined period, and prohibits the sensor circuit 22 from writing data into the memory 24. With this, when the memory 24 stores sufficient encrypted measurement data to be sent to the data communication circuit 20, the data communication circuit 20 can read the encrypted measurement data from the memory 24 and can transmit the encrypted measurement data to a predetermined destination. Thus, the inefficient operation in which the encrypted measurement data is transmitted from the memory 24 with the encrypted measurement data sufficient enough for transmitting to the data communication circuit 20 not stored in the memory 24, for example, when the obtaining request by the data communication circuit 20 is received immediately after the power supply from the power source 23 is turned on can be prevented with a simple structure.

Furthermore, when there has been a response from the sensor circuit 22 within a predetermined period, the memory access control circuit 25 determines that the power source 23 has some power left, and allows the sensor circuit 22 to write the data into the memory 24, and maintains the prohibition on the data communication circuit 20 not to write the data into the memory 24. With this, when it is determined that the power of the power source 23 is left, even when the request for obtaining the encrypted measurement data stored in the memory 24 is received from the data communication circuit 20, the process for storing, into the memory 24, the encrypted measurement data that should be transmitted to the data communication circuit 20 continues. Thus, the inefficient operation in which the encrypted measurement data is transmitted from the memory 24 with the encrypted measurement data sufficient enough for transmitting to the data communication circuit 20 not stored in the memory 24 can be prevented, for example, when the obtaining request by the data communication circuit 20 is received immediately after the power supply from the power source 23 is turned on can be prevented with a simple structure.

Variation 3 of First Embodiment

In the sensor measuring process (S12) illustrated in FIG. 13 in the first embodiment, when the encryption key reading unit 222 cannot obtain the encryption key (S1206 in FIG. 13), the sensor circuit 22 transfers the measured data to the memory access control circuit 25 without encrypting the measured data.

In this variation, when the encryption key reading unit 222 cannot obtain the encryption key, the sensor circuit 22 may discard the measured data, and may not to transfer the measured data to the memory access control circuit 25.

FIG. 23 is a flowchart illustrating the sensor measuring process (S12) according to the variation 3 of the first embodiment. Although each process is similar to the process illustrated in FIG. 7, when the encryption key reading unit 222 cannot obtain the encryption key (No in S1208), the sensor circuit 22 does not perform any process. This discards the measured data, and the measured data will not be transmitted to the memory access control circuit 25.

According to this variation, the unencrypted measurement data is not accumulated on the memory 24. Thus, it is possible to secure the confidentiality of the measured data.

Second Embodiment

The following describes the second embodiment with reference to the drawings. In the first embodiment, the measurement of the biological information by the sensor circuit 22 ends when the measured data reading device 13 requests the sensor tag 2 to obtain the measured data. In the second embodiment, however, the measurement of the biological information by the sensor circuit 22 ends when the measurement of the biological information for a predetermined number of time or predetermined time period by the sensor circuit 22 is performed.

The sensor tag system 1, the sensor tag 2 included in the sensor tag system 1, the encryption key writing device 11, and the measured data reading device 13 have the same structure as described in the first embodiment. Thus, the detailed description for these components is omitted.

In the second embodiment, the measuring process 4 performed by the sensor circuit 22 is partially different from the process described in the first embodiment. The following description shall be made focusing on the differences.

<Operation>

The following describes the process performed by the sensor tag 2 with reference to the drawings.

FIG. 24 is a flowchart illustrating the entire operation of the sensor tag 2. FIG. 24 illustrates the process flow between the sensor circuit 22, the memory access control circuit 25, and the data communication circuit 20, in the same manner as FIG. 8.

The key setting process 3 (S2 to S6) is identical to the same described in the first embodiment. Thus, the detailed description for these components is omitted.

The measuring process 4 starts when the insulator 27 is removed from the sensor tag 2 after the key setting process 3. More specifically, the power supply from the power source 23 is switched on, and the power source status detecting unit 225 detects that the power supply from the power source 23 is on (S38). When it is detected that the power supply from the power source 23 is on, the memory access control circuit 25 changes the memory access control rule (mode) (S40). More specifically, writing the encryption key and ID from the data communication circuit 20 to the memory 24 is prohibited. Furthermore, the memory access control circuit 25 prohibits the data communication circuit 20 from reading encrypted measurement data. The mode change disables any update of the encryption key afterwards (S16, S18, and S20). Furthermore, the encrypted measurement data cannot be obtained (S22, S24, and S28)

When the power supply from the power source 23 is on, the sensor circuit 22 measures the biological information of the person to be measured 12, and outputs the measured data to the memory access control circuit 25 (S42). The memory access control circuit 25 accumulates the output measured data on the memory 24 (S44). Subsequently, the process in S42 and S14 is repeatedly performed for a predetermined number of times. With this process, the measured data for a predetermined number of times is accumulated in the memory 24. Note that the process in S42 and S44 shall be described later in detail.

The sensor measuring process (S42) ends when the predetermined number of measured data is measured. When the sensor measuring process (S42) ends, the data communication circuit 20 is allowed to read the encrypted measurement data, and measured data reading process 5 (S22 to S30) is performed.

<Power Source on Detecting Process (S38)>

Figure 25:
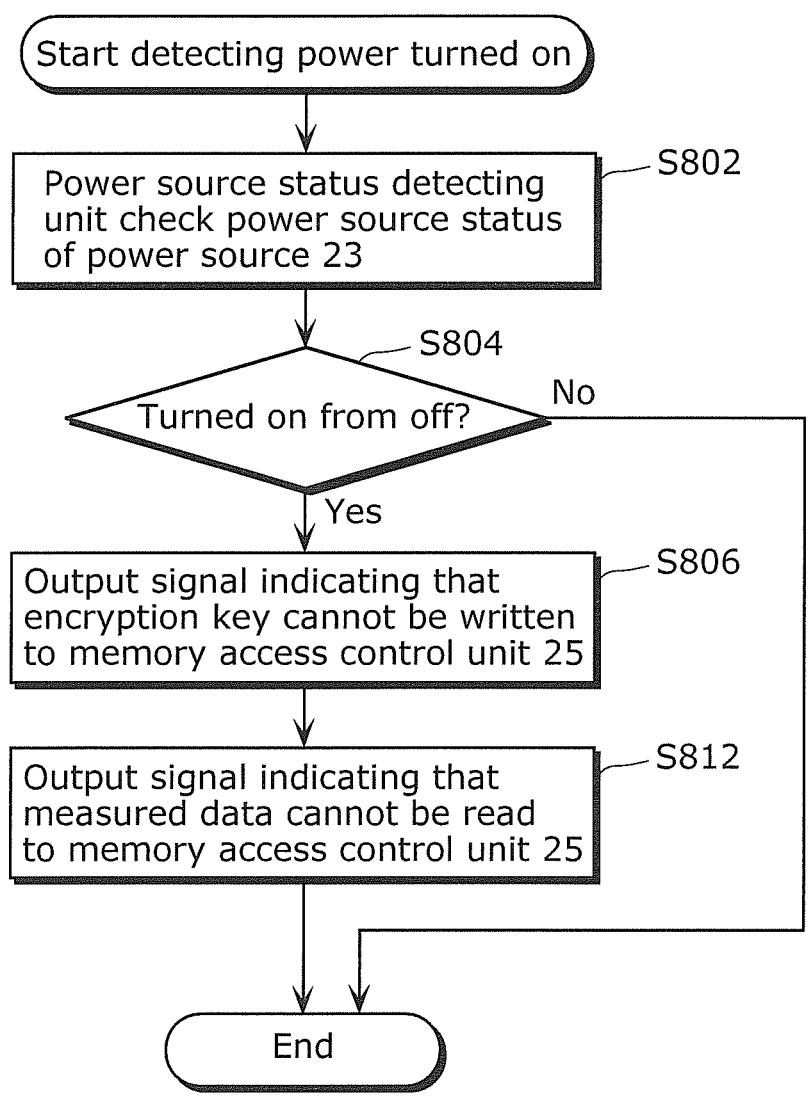
FIG. 25 is a flowchart illustrating power on detection process according to the second embodiment of the present invention in detail.

Next, power source on detecting process (S38) shall be described with reference to FIG. 25.

The process from S802 to S806 is identical to those illustrated in FIG. 11. Thus, the detailed description for the process is omitted here. In addition to the process, in the second embodiment, when it is confirmed that the power supply from the power source 23 changes from off to on (Yes in S804), the power source status detecting unit 225 outputs a signal to the memory access control circuit 25 instructing the memory access control circuit 25 to prohibit the data communication circuit 20 from reading the encrypted measurement data on the memory 24 (S812).

<Mode Changing Process (S40)>

Figure 26:
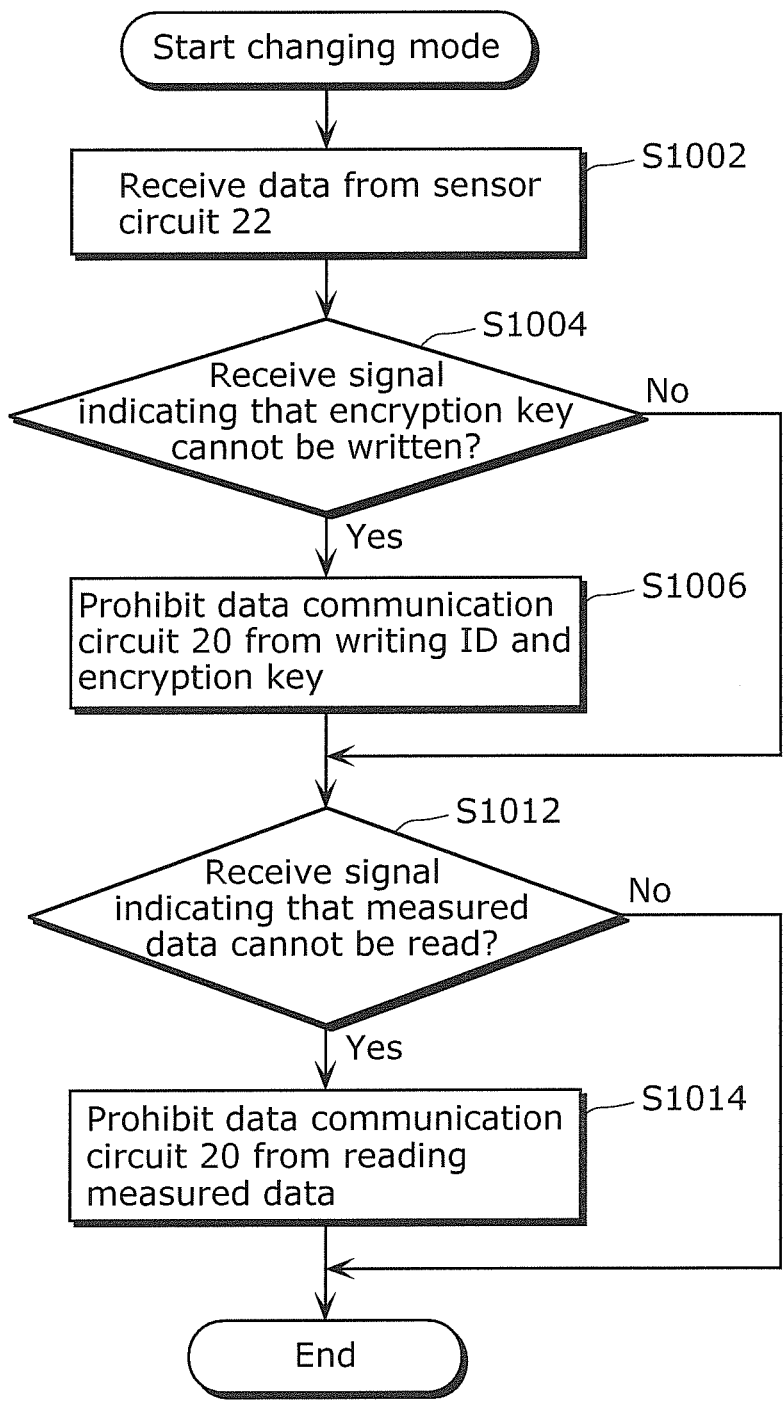
FIG. 26 is a flowchart illustrating a mode change process according to the second embodiment of the present invention in detail.

The mode changing process (S40) shall be described with reference to FIG. 26.

The process from S1002 to S1006 is identical to those illustrated in FIG. 12. Thus, the detailed description for the process is omitted here. In the second embodiment, after the process in S1006, the memory access control circuit 25 determines whether or not the signal indicating that the measured data cannot be read is received or not (S1012). When the signal indicating that the measured data cannot be read is received (Yes in S1012), the memory access control rule updating unit 26 changes the memory access control rule (mode) to prohibit the data communication circuit 20 from reading the encrypted measurement data in the memory 24 (S1014). More specifically, the memory access control rule updating unit 26 updates the memory access control rule set in the memory access control circuit 25 to allow the following memory accesses only and denies the other memory accesses.

(4) Reading the Encryption Key from the Sensor Circuit 22
(5) Writing encrypted measurement data from the sensor circuit 22

As described above, with the update on the memory access control rule, the encrypted measurement data cannot be obtained afterwards (S22, S24, and S28).

<Sensor Measuring Process (S42)>

Figure 27:
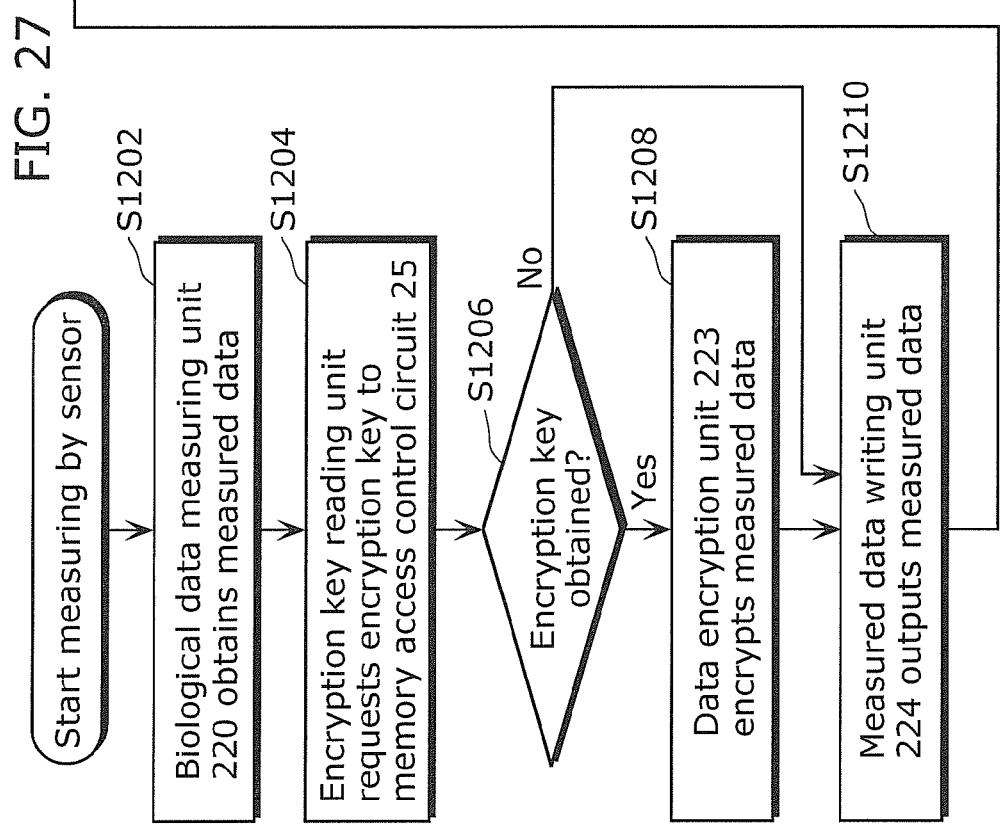
FIG. 27 is a flowchart illustrating sensor measuring process according to the second embodiment of the present invention in detail

The sensor measuring process (S42) shall be described with reference to FIG. 27.

The process from S1202 to S1210 is identical to those illustrated in FIG. 13. Thus, the detailed description for the process is omitted here. In the second embodiment, after S1210, the biological data measuring unit 220 further increments the measurement count stored inside by one (S1212). Note that, the measurement count is set to 0 when the measurement starts.

The biological data measuring unit 220 determines whether or not the current measurement count exceeds the predetermined threshold (S1214). When it is determined that the current measurement count exceeds the threshold (Yes in S1214), the biological data measuring unit 220 stops measuring the biological information (S1216). Furthermore, the measured data writing unit 224 outputs, to the memory access control circuit 25, the measurement end signal indicates that the measurement of the biological information ended (S1218). With this, after the biological information is measured for a predetermined number of times, the measurement of the biological information ends. Note that, the memory access control circuit 25 may stop storing the encrypted measurement data on the memory 24, instead of the sensor circuit 22 ending the measurement.

<Measured Data Accumulating Process (S44)>

The measured data accumulating process (S44) shall be described with reference to FIG. 28.

The process from S1402 to S1410 is identical to those illustrated in FIG. 14. Thus, the detailed description for the process is omitted here. In the second embodiment, after S1410, the memory access control circuit 25 further determines whether or not the measurement ending signal is received (S1412). When it is determined that the measurement ending signal is received (Yes in S1412), the memory access control rule updating unit 26 changes the memory access control rule (mode) such that the sensor circuit 22 is prohibited from writing the encrypted measurement data and the data communication circuit 20 is allowed to read the encrypted measurement data (S1413, S1414). More specifically, the memory access control rule updating unit 26 updates the memory access control rule set in the memory access control circuit 25 to allow the following memory accesses only and denies the other memory accesses.

(3) Reading the Encrypted Measurement Data from the Data Communication Circuit 20
(4) Reading the Encryption Key from the Sensor Circuit 22

With this, when the measurement of the biological information ends, the encrypted measurement data in the memory 24 is not updated, and the data communication circuit 20 can read the encrypted measured data.

Note that, in the second embodiment, the measurement of the biological information ends when the measurement count exceeds a predetermined threshold. However, the ending condition is not limited to this. For example, the biological data measuring unit 220 in the sensor circuit 22 may monitor the timer data (count value) of the timer unit 221, and the measurement of the biological information may end when the count value exceeds a predetermined threshold. Alternatively, the timer unit 221 may manage the time from the start of the measurement, and the biological data measuring unit 220 may monitor the time from the start of the measurement. When the time exceeds the predetermined threshold, the measurement of the biological information may end.

As described above, the second embodiment achieves the same effect as the first embodiment.

Furthermore, when the data communication circuit 20 is reading the encrypted measurement data, the sensor circuit 22 does not write data on the memory 24. Thus, it is possible to prevent the encrypted measurement data stored in the memory 24 from leaking.

<Variation>

Needless to say, the present invention is not limited to the embodiments. For example, the present invention includes the following cases.

(1) The encryption scheme used for encryption and decryption is not limited to a particular algorithm. The encryption scheme may be a public key cryptography such as the Rivest Shamir Adleman (RSA), the Elliptic Curve Cryptography, or the ElGamal encryption system. Alternatively, the encryption scheme may also be a common key cryptosystem such as the Advanced Encryption Standard (AES), or the Data Encryption Standard (DES). The data size of each data, and the number of data items are not limited to a specific size or the number.

(2) The data to be encrypted is not limited to the data described in the embodiments. For example, counter information which indicates what number is the measured data after the measurement is started is recorded with the measured data, and the counter information may be encrypted as well. Furthermore, the data written on the sensor tag 2 is not limited to the data measured by the sensor tag 2. For example, personal information such as the name, address, and phone number of the patient may be written. In this case, the personal information may be encrypted by the key that is set.

(3) The sensor tag 2 may include two or more types of sensor circuits. In other words, the sensor tag 2 may measure two or more types of data and store the measured data inside the sensor tag 2. In this case, a sensor type ID for identifying the type of the measured data may be added and stored together with the measured data. Furthermore, depending on the type of the measured data, the setting may be adjusted such that the data is stored with or without encryption. Furthermore, the rule for determining whether or not the measured data is encrypted, depending on the type of the measured data, may be set from outside. The rule may be set at the time of setting the key, or may be changed by an instruction from outside during the measurement.

(4) Although the number of encryption key that can be set on the sensor tag 2 is one in the embodiments above, multiple encryption keys may be set on the sensor tag 2. In this case, the encryption key used for encrypting the measured data may be set depending on the type of the measured data, or the encryption key may be changed depending on the time and place of measuring the measurement data. Furthermore, the rule for determining the encryption key to be used may be obtained within the sensor tag 2, or may be obtained from outside the sensor tag 2.

(5) Methods for the sensor tag 2 to authenticate the validity of the encryption key writing device 11 and the measured data reading device 13 are not limited to the method using the hash value as described above, and may be a challenge-response type authentication using the common key cryptosystem or the public key cryptography. Furthermore, the communication data between the sensor tag 2 and the encryption key writing device 11 or the measured data reading device 13 may be encrypted using the Secure Socket Layer (SSL). Furthermore, at the time of measured data reading process, there may be multiple authentication methods for the sensor tag 2 to authenticate the measured data reading device 13, and the measured data reading device 13 may change the information obtained from the sensor tag 2. Furthermore, when there are multiple measured data reading devices, the information given by the sensor tag 2 may be changed for each device.

(6) The sensor tag 2 measures the biological information by the biological data measuring unit 220 in the sensor circuit 22. However, the function of measuring the biological information may be performed by the device other than the sensor tag 2. In this case, in addition to the sensor tag 2, there is biological information measuring device, for example. The biological information measuring device transmits the measured biological data to the sensor tag 2 via wireless communication and others. The receiving circuit 28 in the sensor tag 2 receives the transmitted biological data. In this case, the sensor tag 2 may be used as the sensor tag 2 separate from the biological information measuring device.

(7) As an application example of the sensor tag system 1, it is described that the hospital manages the encryption key writing device 11 and the measured data reading device 13, and provides the patient with the sensor tag 2 with the encryption key set. However, the application is not limited to this model. For example, the patient may manage the encryption key writing device 11 and the measured data reading device 13 such that the patient can set the encryption key uniquely determined for the patient on the sensor tag 2.

(8) The encryption key writing device 11 and the measured data reading device 13 may be connected to the server via the network. Here, the server holds the encryption key and the decryption key. When setting the encryption key on the sensor tag 2, or when reading the encrypted measurement data from the measured sensor tag 2 and decrypting the data, the encryption key writing device 11 and the measured data reading device 13 may obtain the encryption key and the decryption key from the server.

(9) The sensor tag 2 may not only encrypt the measured data, but also generate falsification detection data of the measured data. The known Message Authentication Code (MAC) using an encryption key may be used as the method for generating the falsification detection data.

(10) The sensor tag system 1 is not limited to the use case of measuring the biological information. For example, the sensor tag system 1 may be used for managing the environment of fresh food during transportation. In this case, the sensor tag 2 is set on the fresh food or a container holding the fresh food, and temperature, humidity, and illuminance during the transportation are measured and accumulated. In addition, the sensor circuit 22 is an acceleration sensor or a Global Positioning System (GPS) reception module, and the sensor tag system 1 may be used as an action tracking system measuring the position history and the traveling speed. In this case, the positional history and traveling speed of the person to be measured who is wearing the sensor tag 2 can be encrypted, and recorded in the sensor tag 2. Furthermore, the present invention is not limited to the tag with the sensor function. For example, it may be an authentication tag which performs a challenge-response authentication using the encryption key that is set. In other words, the present invention is applicable to an encryption device which performs encryption inside the device, and that the encryption key used for the encryption can be set from outside.

(11) Although the power supply from the power source 23 to the sensor circuit 22 is turned on from off by removing the attached insulator 27, it is not limited to this example. For example, magnetic switch or infrared switch may turn on the power supply from the power source 23 to the sensor circuit 22 from off.

(12) Non-contact wireless communication through the antenna 21 is used when the measured data reading device 13 reads the measured data from the sensor tag 2. However, it is not limited to this example, and contact communication may be used. Furthermore, power supply when reading data is not limited to the supply from the activation signal from the measured data reading device 13. The power may be supplied from the power source 23 embedded to the sensor tag 2.

(13) When setting the encryption key on the sensor tag 2, the encryption key writing device 11 may hold, inside the encryption key writing device 11, the encryption key set to the sensor tag 2, or the encryption key may be input from outside of the device. Furthermore, the encryption key writing device 11 may be connected to the encryption key management device through the network when setting the encryption key, receive the encryption key from the encryption key management device, and set the encryption key on the sensor tag

(14) At the time of measured data reading process from the sensor tag 2, the measured data reading device 13 may connect to the sensor tag 2 through a network such as the Internet, and read the group of encrypted measurement data.

(15) The method for updating the memory access control rule of the memory access control circuit 25 when the power is supplied from the power source 23 to the sensor circuit 22 is not limited to the methods described in the embodiments. For example, suppose there are two or more memory access control circuits with different memory access control rule, the access control circuit to be used may be switched when the power is supplied from the power source 23 to the sensor circuit 22. Alternatively, the signal line for writing the encryption key may be disconnected by removing the insulator 27, making it impossible to physically write the encryption key.

(16) When the power supply from the power source 23 to the sensor circuit 22 is supplied from not supplied due to the consumed power and the power supply from the power source turned off, the status may be switched from "the encryption key cannot be written" to "the encryption key can be written".

(17) Each of the devices is a computer system including a microprocessor, a ROM, a RAM, a hard disk unit, a display unit, a keyboard, and a mouse. A computer program is recorded on the RAM or the hard disk unit. Functions of each device are achieved through the operation of the microprocessor according to the computer program. The computer program is configured of a combination of command codes indicating instructions to the computer for achieving the predetermined functions.

(18) A part or all of the constituent elements constituting the respective devices may be configured from a single System-Large-Scale Integration (LSI). The system LSI is an ultra multi-function LSI having multiple components integrated into one chip, and more specifically, is a computer system that includes a microprocessor, a ROM, and a RAM and others. A computer program is recorded on the RAM. Functions of the system LSI are achieved through the operation of the microprocessor according to the computer program.

(19) A part or all of the constituent elements constituting the respective devices may be configured as an IC card which can be detachably attached and detached from the respective apparatuses or as a stand-alone module. The IC card or the module is a computer system configured of a microprocessor, a ROM, and a RAM and others. The IC card and the module may include the ultra multi-function LSI. Functions of the IC card or the module are achieved through the operation of the microprocessor according to the computer program. The IC card or the module may be tampering-resistant.

(20) The present invention may be a method described above. Furthermore, the present invention may be a computer program which implements these methods by a computer, or digital signals composed of the computer program.

Furthermore, the present invention may be a computer-readable recording medium storing the computer program or the digital signals. The recording medium may be, for example, a flexible disk, a hard disk, a CD-ROM, an MO, a DVD, a DVD-ROM, a DVD-RAM, a Blu-ray Disc (BD), or a semiconductor memory. Furthermore, it may be the digital signal recorded on the recording medium.

Furthermore, the present invention may be the computer program or the digital signals transmitted through a telecommunication line, wireless or wired communication line, a network such as the Internet, or data broadcast.

The present invention may be a computer system including a microprocessor and a memory, and the memory may store the computer program, and the microprocessor may operate according to the computer program.

Furthermore, the program or the digital signals may be implemented in another independent computer system through recording the program and the digital signals on the recording medium and transferring the program and digital signals.

(21) The embodiments and the variations may be combined.

Although only an exemplary embodiment of the telemedical system according to this invention has been described in detail above, those skilled in the art will readily appreciate that many modifications are possible in the exemplary embodiment without materially departing from the novel teachings and advantages of this invention. Accordingly, all such modifications are intended to be included within the scope of this invention.

The sensor tag according to the present invention has a feature that allows setting encryption key without wasting the embedded battery even when a free on/off mechanism for power supply from the embedded battery cannot be implemented. Thus, it is useful for implementing a sensor tag required for encrypting the sensor information accumulated under strict conditions for the capacity of battery and implementation size.

The invention claimed is:

1. A portable data encryption device, comprising:
   a storage;
   a primary cell including a power supply that is off in an initial state and that supplies power when switched on;
   a wireless communication circuit which receives a wireless activation signal from an external terminal, and, in an operation using electromotive force generated by the received activation signal when the power supply from the primary cell is off, receives an encryption key from the external terminal and stores the received encryption key in the storage;
   a switch which switches the power supply of the primary cell from off to on after the encryption key is stored in the storage by the wireless communication circuit;
   an encryption circuit which reads the encryption key from the storage, encrypts data using the read encryption key, and stores the encrypted data in the storage, the encryption circuit operating using the power supplied from the primary cell after the power supply from the primary cell is switched on; and
   a storage control unit configured to control access by the wireless communication circuit to the storage and access by the encryption circuit to the storage,
   wherein the storage control unit prohibits the wireless communication circuit from writing the encryption key in the storage, when the encryption circuit operates using the power supplied from the primary cell, and
   the switch switches the power supply from the primary cell one way from off to on.

2. The data encryption device according to claim 1, wherein the encryption circuit, which is a sensor circuit, measures biological data of a user of the data encryption device, reads the encryption key from the storage, encrypts the biological data using the read encryption key, and stores encrypted biological data in the storage.

3. The data encryption device according to claim 1, further comprising
   an input unit configured to receive, as an input, biological data of a user from an external measuring device which measures the biological data,
   wherein the encryption circuit encrypts the biological data as the data, and stores the encrypted biological data in the storage.

4. The data encryption device according to claim 1,
wherein, when the power supply from the primary cell is switched on and the encryption circuit operates using the power supplied from the primary cell, with the encryption key not being stored in the storage, the encryption circuit stores the data in the storage without encryption.

5. The data encryption device according to claim 1,
wherein, when the power supply from the primary cell is switched on and the encryption circuit operates using the power supplied from the primary cell, with the encryption key not being stored in the storage, the encryption circuit discards the data, and does not store the data in the storage.

6. The data encryption device according to claim 1,
wherein the primary cell and the encryption circuit are urged toward each other, and
the switch is an insulator interposed between the urged primary cell and the urged encryption circuit.

7. The data encryption device according to claim 1,
wherein the data is personal information of a user of the data encryption device.

8. The data encryption device according to claim 1,
wherein the encryption circuit is a sensor circuit which measures environment information around an item to which the data encryption device is attached, reads the encryption key from the storage, encrypts the environment information using the read encryption key, and stores the encrypted environment information in the storage.

9. The data encryption device according to claim 1,
wherein the wireless communication circuit is a Radio Frequency Identification (RFID) communication circuit.

10. The data encryption device according to claim 1, further comprising
an indicator configured to display an indication that the encryption key is stored in the storage.

11. The data encryption device according to claim 1, further comprising
a storage control unit configured to control an access by the wireless communication circuit to the storage and an access by the encryption circuit to the storage,
wherein, when the encryption circuit operates using the power supplied from the primary cell, the storage control unit is configured to allow the encryption circuit to write data in the storage, and to prohibit the wireless communication circuit from writing data in the storage,
the encryption circuit is a sensor circuit, and measures biological data of a user of the data encryption device, reads the encryption key from the storage, encrypts the biological data using the read encryption key, and stores encrypted biological data in the storage,
the storage control unit is configured to prohibit the encryption circuit from writing the data in the storage when a request for obtaining the encrypted data stored in the storage is received from the wireless communication circuit, and
the wireless communication circuit transmits the encrypted data stored in the storage to a predetermined destination, after the storage control unit prohibits the encryption circuit from writing the data in the storage.

12. The data encryption device according to claim 11,
wherein, when the request for obtaining the encrypted data stored in the storage is received from the wireless communication circuit, the storage control unit is configured to determine whether or not the encryption circuit has written the data in the storage within a predetermined period, and to prohibit the encryption circuit from writing the data in the storage when it is determined that the encryption circuit has not written the data in the storage in the predetermined period.

13. The data encryption device according to claim 12,
wherein, when the request for obtaining the encrypted data stored in the storage is received from the wireless communication circuit, the storage control unit is configured to determine whether or not the encryption circuit has written the data in the storage within a predetermined period, and when it is determined that the encryption circuit has written the data in the storage within the predetermined period, the storage control unit is configured to allow the encryption circuit to write the data in the storage, and to maintain the prohibition against writing the data in the storage by the wireless communication circuit.

14. The data encryption device according to claim 12,
wherein, when the request for obtaining the encrypted data stored in the storage is received from the wireless communication circuit, the storage control unit is configured to output, to the encryption circuit, a predetermined signal for confirming that the encryption circuit is in operation, and determines whether or not the encryption circuit has responded within a predetermined period, and the storage control unit prohibits the encryption circuit from writing the data in the storage when it is determined that the response has not received within the predetermined period.

15. The data encryption device according to claim 14,
wherein, when the request for obtaining the encrypted data stored in the storage is received from the wireless communication circuit, the storage control unit is configured to output, to the encryption circuit, a predetermined signal for confirming that the encryption circuit is in operation, and determines whether or not the encryption circuit has responded within a predetermined period, and when it is determined that the response has received within the predetermined period, the storage control unit is configured to allow the encryption circuit to write the data in the storage, and to maintain the prohibition against writing the data in the storage by the wireless communication circuit.

16. The data encryption device according to claim 1, further comprising
a storage control unit configured to control an access by the wireless communication circuit to the storage and an access by the encryption circuit to the storage,
wherein, when the encryption circuit operates using the power supplied from the primary cell, the storage control unit is configured to allow the encryption circuit to write data in the storage, and to prohibit the wireless communication circuit from writing data in the storage,
the encryption circuit is a sensor circuit which measures biological data of a user of the data encryption device, reads the encryption key from the storage, encrypts the biological data using the read encryption key, stores encrypted biological data in the storage, and when the biological data is measured for a predetermined number of times, notifies of the storage control unit that the biological data has been measured for the predetermined number of times,
the storage control unit is configured to prohibit the encryption circuit from writing the data in the storage when the notification that the biological data has been measured for the predetermined number of times is received, and the wireless communication circuit transmits the encrypted data stored in the storage to a predetermined destination, after the storage control unit prohibits the encryption circuit from writing the data in the storage.

17. The data encryption device according to claim 1, further comprising
a storage control unit configured to control an access by the wireless communication circuit to the storage and an access by the encryption circuit to the storage,
wherein, when the encryption circuit operates using the power supplied from the primary cell, the storage control unit is configured to allow the encryption circuit to write data in the storage, and to prohibit the wireless communication circuit from writing data in the storage,
the encryption circuit is a sensor circuit, and measures biological data of a user of the data encryption device, reads the encryption key from the storage, encrypts the biological data using the read encryption key, and stores encrypted biological data in the storage,
the storage control unit is configured to prohibit the encryption circuit from writing the data in the storage after a predetermined time has passed since the power supply from the primary cell has switched on, and
the wireless communication circuit transmits the encrypted data stored in the storage to a predetermined destination, after the storage control unit prohibits the encryption circuit from writing the data in the storage.

18. A control method for a portable data encryption device, the control method comprising:
receiving a wireless activation signal from an external terminal by a wireless communication circuit of the portable data encryption device, the wireless communication circuit operating using electromotive force generated by the received activation signal when a power supply of a primary cell of the portable data encryption device is off;
receiving an encryption key from the external terminal by the wireless communication circuit and storing the received encryption key by the wireless communication circuit in a storage of the portable data encryption device, when the power supply from the primary cell is off;
switching the power supply from the primary cell from off to on by a switch of the portable data encryption device after the encryption key is stored in the storage by the wireless communication circuit, the power supply supplying power when switched on from an initial off state; and
prohibiting the wireless communication circuit from writing the encryption key in the storage when an encryption circuit of the portable data encryption device operates using the power supplied from the primary cell, reading the encryption key by the encryption circuit from the storage after the power supplied from the primary cell is switched on from off by the switch, encrypting data by the encryption circuit, and storing the encrypted data by the encryption circuit in the storage,
wherein the switch switches the power supply from the primary cell one way from off to on.

19. A portable integrated circuit, comprising:
a storage;
a primary cell including a power supply that is off in an initial state and that supplies power when switched to an on state;
a wireless communication circuit which receives a wireless activation signal from an external terminal, and, in an operation using electromotive force generated by the received activation signal when the power supply from the primary cell is off, receives an encryption key from the external terminal and stores the received encryption key in the storage;
a switch which switches the power supply from the primary cell from off to on after the encryption key is stored in the storage by the wireless communication circuit;
an encryption circuit which reads the encryption key from the storage, encrypts data using the read encryption key, and stores the encrypted data in the storage, the encryption circuit operating using the power supplied from the primary cell after the power supply from the primary cell is switched on; and
a storage control unit configured to control access by the wireless communication circuit to the storage and access by the encryption circuit to the storage,
wherein the storage control unit prohibits the wireless communication circuit from writing the encryption key in the storage, when the encryption circuit operates using the power supplied from the primary cell, and
the switch switches the power supply from the primary cell one way from off to on.

* * * * *